US010717965B2

(12) United States Patent
Gilbert et al.

(10) Patent No.: US 10,717,965 B2
(45) Date of Patent: Jul. 21, 2020

(54) MAMMALIAN CELL CULTURE-PRODUCED NEUBLASTIN ANTIBODIES

(71) Applicant: GLORIANA THERAPEUTICS SARL, Providence, RI (US)

(72) Inventors: Alan Gilbert, Cambridge, MA (US); Kyle McElearney, Medford, MA (US); Terrence Michael Dobrowsky, Cambridge, MA (US); Rashmi Rohit Kshirsagar, Ashland, MA (US)

(73) Assignee: Gloriana Therapeutics, Inc., Providence, RI (US)

( * ) Notice: Subject to any disclaimer, the term of this patent is extended or adjusted under 35 U.S.C. 154(b) by 0 days.

(21) Appl. No.: 16/230,216

(22) Filed: Dec. 21, 2018

(65) Prior Publication Data

US 2019/0194602 A1 Jun. 27, 2019

Related U.S. Application Data

(63) Continuation-in-part of application No. 15/291,257, filed on Oct. 12, 2016, now abandoned, which is a continuation of application No. 14/760,182, filed as application No. PCT/US2014/011130 on Jan. 10, 2014, now abandoned.

(60) Provisional application No. 61/751,067, filed on Jan. 10, 2013.

(51) Int. Cl.

| | |
|---|---|
| ***C12N 5/00*** | (2006.01) |
| ***C12P 21/00*** | (2006.01) |
| ***C07K 16/22*** | (2006.01) |
| ***C07K 14/755*** | (2006.01) |

(52) U.S. Cl.

CPC .......... *C12N 5/0018* (2013.01); *C07K 14/755* (2013.01); *C07K 16/22* (2013.01); *C12P 21/00* (2013.01); *C12N 2500/24* (2013.01); *C12N 2500/30* (2013.01); *C12N 2500/34* (2013.01); *C12N 2511/00* (2013.01)

(58) Field of Classification Search

None

See application file for complete search history.

(56) References Cited

U.S. PATENT DOCUMENTS

| | | | |
|---|---|---|---|
| 4,560,655 | A | 12/1985 | Baker |
| 4,657,866 | A | 4/1987 | Kumar |
| 4,683,195 | A | 7/1987 | Mullis et al. |
| 4,767,704 | A | 8/1988 | Cleveland et al. |
| 4,927,762 | A | 5/1990 | Darfler |
| 5,122,469 | A | 6/1992 | Mather et al. |
| 5,223,409 | A | 6/1993 | Ladner et al. |
| 5,225,539 | A | 7/1993 | Winter |
| 5,585,089 | A | 12/1996 | Queen et al. |
| 5,658,727 | A | 8/1997 | Barbas et al. |
| 5,667,988 | A | 9/1997 | Barbas et al. |
| 5,693,761 | A | 12/1997 | Queen et al. |
| 5,693,762 | A | 12/1997 | Queen et al. |
| 5,859,205 | A | 1/1999 | Adair et al. |
| 5,869,046 | A | 2/1999 | Presta et al. |
| 5,885,793 | A | 3/1999 | Griffiths et al. |
| 6,407,213 | B1 | 6/2002 | Carter et al. |
| 7,064,244 | B2 | 6/2006 | Jakobovits et al. |
| 7,348,004 | B2 | 3/2008 | Peters et al. |
| 7,355,008 | B2 | 4/2008 | Stavenhagen et al. |
| 7,404,945 | B2 | 7/2008 | Ito et al. |
| 7,404,956 | B2 | 7/2008 | Peters et al. |
| 7,785,880 | B2 | 8/2010 | Goldenberg et al. |
| 7,820,162 | B2 | 10/2010 | Mezo et al. |
| 7,862,820 | B2 | 1/2011 | Peters et al. |
| 8,329,182 | B2 | 12/2012 | Peters et al. |
| 2003/0070185 | A1 | 4/2003 | Jakobovits et al. |
| 2005/0079574 | A1 | 4/2005 | Bond |
| 2009/0280533 | A1 | 11/2009 | Gorfien et al. |
| 2015/0344550 | A1 | 12/2015 | Rossomando et al. |
| 2017/0130191 | A1 | 5/2017 | Pla et al. |

FOREIGN PATENT DOCUMENTS

| | | | |
|---|---|---|---|
| WO | WO 198700195 | A1 | 1/1987 |
| WO | WO 198705330 | A1 | 9/1987 |
| WO | WO 199002809 | A1 | 3/1990 |
| WO | WO 199003430 | A1 | 4/1990 |
| WO | WO 199117271 | A1 | 11/1991 |
| WO | WO 199201047 | A1 | 1/1992 |
| WO | WO 199209690 | A2 | 6/1992 |
| WO | WO 199215679 | A1 | 9/1992 |
| WO | WO 199218619 | A1 | 10/1992 |
| WO | WO 199220791 | A1 | 11/1992 |
| WO | WO 199301288 | A1 | 1/1993 |

(Continued)

OTHER PUBLICATIONS

Rudikoff et al (Proc Natl Acad Sci USA 1982 vol. 79 (Year: 1982).*
MacCallum et al. J. Mol. Biol. (1996) 262, 732-745 (Year: 1996).*
Pascalis et al. The Journal of Immunology (2002) 169, 3076-3084 (Year: 2002).*
Casset et al. (2003) BBRC 307, 198-205 (Year: 2003).*
Vajdos et al. (2002) 320, 415-42 (Year: 2002).*
Holm et al. (2007) 44, 1075-1084 (Year: 2007).*
Chen et al. J. Mol. Bio. (1999) 293, 865-881 (Year: 1999).*
Wu et al. J. Mol. Biol. (1999) 294, 151-162 (Year: 1999).*
American Type Culture Collection Catalogue of Cell Lines and Hybridomas, Sixth Edition, 1988, pp. 346-349 (7 pages).
Angal et al. (1993) A single amino acid substitution abolishes the heterogeneity of chimeric mouse/human (IgG4) antibody. Mol. Immunol, 30(1):105-108.

(Continued)

*Primary Examiner* — Kimberly Ballard
*Assistant Examiner* — Stacey N MacFarlane
(74) *Attorney, Agent, or Firm* — Lathrop GPM LLP; Ann-Louise Kerner

(57) ABSTRACT

The present disclosure pertains to a mammalian cell culture genetically modified to express, and which expresses, a neublastin antibody polypeptide, or fragment thereof, in the culture, and to a neublastin antibody polypeptide, or fragment thereof, made by a mammalian cell culture genetically modified to express, and which expresses, the neublastin antibody polypeptide, or fragment thereof.

17 Claims, 17 Drawing Sheets

Specification includes a Sequence Listing.

(56) References Cited

FOREIGN PATENT DOCUMENTS

| | | | |
|---|---|---|---|
| WO | WO 199633735 | A1 | 10/1996 |
| WO | WO 199634096 | A1 | 10/1996 |
| WO | WO 2002040544 | A2 | 5/2002 |
| WO | WO 2003020764 | A2 | 3/2003 |
| WO | WO 2007149406 | A2 | 12/2007 |
| WO | WO 2008118507 | A2 | 10/2008 |
| WO | WO 2009130198 | A2 | 10/2009 |
| WO | WO 2009137254 | A2 | 11/2009 |
| WO | WO 2009140015 | A2 | 11/2009 |
| WO | WO 2011069164 | A2 | 6/2011 |
| WO | WO 2012006623 | A1 | 1/2012 |
| WO | WO 2012006624 | A2 | 1/2012 |
| WO | WO 2012006633 | A1 | 1/2012 |
| WO | WO 2012006635 | A1 | 1/2012 |

OTHER PUBLICATIONS

Aplin et al. (1981) Preparation, Properties, and Applications of Carbohydrate Conjugates of Proteins and Lipids. CRC Crit. Rev. Biochem. 10(4):259-306.
Bai et al. (2011) Role of iron and sodium citrate in animal protein-free CHO cell culture medium on cell growth and monoclonal antibody production. Biotechnol. Prog. 27:209-219.
Barnes et al. (1980) Methods for growth of cultured cells in serum-free medium. Anal. Biochem. 102:255-270.
Berge et al. (1977) Pharmaceutical salts, J. Pharm. Sci. 66(1):1-19.
Brunetti-Pierri et al. (2009) Bioengineered Factor IX Molecules with Increased Catalytic Activity Improve the Therapeutic Index of Gene Therapy Vectors for Hemophilia B. Human Gene Therapy 20:479-485.
Hang et al. (1998) Changing Residue 338 in Human Factor IX from Arginine to Alanine Causes an Increase in Catalytic Activity, J. Biolog. Chem. 273(20):12089-12094.
Chiang et al. (2005) Bcl-xL mediates increased production of humanized monoclonal antibodies in Chinese hamster ovary cells. Biotechnol. & Bioengineer. 91(7):779-792.
Davies et al. (1996) Single antibody domains as small recognition units: design and in vitro antigen selection of camelized, human VH domains with improved protein stability. Protein Eng. 9(6):531-537.
De Vries et al. (1992) The fms-like tyrosine kinase, a receptor for vascular endothelial growth factor. Science 255:989-991.
Edge, A. (2003) Deglycosylation of glycoproteins with trifluoromethanesulfonic acid: elucidation of molecular structure and function., J. Biochem. 376:339-350.
Final Office Action for U.S. Appl. No. 14/760,182 dated May 24, 2017.
Green et al. (1994) Antigen-specific human monoclonal antibodies from mice engineered with human Ig heavy and light chain YACs. Nature Genetics 7:13-21.
Ham et al. (1979) Media and growth requirements. Meth. Enzymol., 58:44-93.
Huang et al. (2010) Maximizing productivity of CHO cell-based fed-batch culture using chemically defined media conditions and typical manufacturing equipment. Biotechnol. Prog. 26:1400-1410.
Johnson et al. (1980) Localization of mitochondria in living cells with rhodamine 123. Proc. Natl. Acad. Sci. USA. 77(2):990-994.
Kovar, et al., (1987) "Iron Compounds at High Concentrations Enable Hybridoma Growth in a Protein-Fee Medium," Biotechnology Letters, 9(4):259-264.
Luo et al. (2007) Combined approach of NMR and chemometrics for screening peptones used in the cell culture medium for the production of a recombinant therapeutic protein. Biotechnol. & Bioengineer, 97(6):1654-1659.
Ma et al. (2009) A single nutrient feed supports both chemically defined NSO and CHO fed-batch processes: Improved productivity and lactate metabolism. Biotechnol. Prog. 25:1353-1363.
Mather et al. (1982) Culture of testicular cells in hormone-supplemented serum-free medium. Ann. N.Y. Acad. Sci., 383:44-68.
Milstein et al. (1983) Hybrid hybridomas and their use in immunohistochemistry. Nature 305:537-540.
Morrison, S. L. (1985) Transfectomas provide novel chimeric antibodies. Science 229:1202-1207.
Mustonen et al. (1995) Endothelial receptor tyrosine kinases involved in angiogenesis. J. Cell Biol. 129:895-898.
Oi et al. (1986) Chimeric antibodies. BioTechniques 4(3):214-221.
Omasa et al. (2010) Enhanced antibody production following intermediate addition based on flux analysis in mammalian cell continuous culture. Bioproc. & Biosyst. Eng. 33:117-125.
Persson et al. (2001a) Rational design of coagulation factor Vila variants with substantially increased intrinsic activity. PNAS 98(24):13583-13588.
Persson et al. (2001b) Substitution of Valine for Leucine 305 in Factor Vila Increases the Intrinsic Enzymatic Activity. J. Biol. Chem. 276(31):29195-29199.
Petrovan et al. (2001) Residue Met156 Contributes to the Labile Enzyme Conformation of Coagulation Factor Vila. J. Biol. Chem. 276(9):6616-6620.
Pham et al. Large-Scale Transient Transfection of Serum-Free Suspension-Growing HEK293 EBNA1 Cells: Peptone Additives Improve Cell Growth and Transfection Efficiency, Biotechnology and Bioengineering, vol. 84, No. 3, Nov. 5, 2003.
Porter et al. (2010) Strategies for selecting recombinant CHO cell lines for cGMP manufacturing: realizing the potential in bioreactors. Biotechnol. Prog. 26:1446-1454.
Sato et al. (1995) Distinct roles of the receptor tyrosine kinases Tie-1 and Tie-2 in blood vessel formation. Nature 376:70-74.
Shibuya et al. (1990) Nucleotide sequence and expression of a novel human receptor-type tyrosine kinase gene (fit) closely related to the fms family. Oncogene 5:519-524.
Sichler et al. (2003) Physiological fIXa Activation Involves a Cooperative Conformational Rearrangement of the 99-Loop. J. Biol. Chem. 278(6):4121-4126.
Smith, G.P. (1985) Filamentous fusion phage: novel expression vectors that display cloned antigens on the virion surface. Science 228:1315-1317.
Soejima et al. (2002) The 99 and 170 loop-modified factor Vila mutants show enhanced catalytic activity without tissue factor, J. Biol. Chem. 277(50):49027-49035.
Soejima et al. (2001). Factor Vila modified in the 170 loop shows enhanced catalytic activity but does not change the Eymogen-like property, J. Biol. Chem. 276(20):17229-17235.
Sojar et al. (1987) A chemical method for the deglycosylation of proteins. Arch. Biochem. Biophys. 259(1):52-57.
Sturzebecher et al. (1997) Dramatic enhancement of the catalytic activity of coagulation factor IXa by alcohols. FEBS Lett. 412:295-300.
Terman et al. (1991) Identification of a new endothelial cell growth factor receptor tyrosine kinase. Oncogene 3:1677-1683.
Thotakura et al. (1987) Enzymatic deglycosylation of glycoproteins. Meth. Enzymol. 138:350-359.
Ullrich et al. (1990) Signal transduction by receptors with tyrosine kinase activity. Cell 61:203-212.
Yarden et al. (1988) Growth factor receptor tyrosine kinases. Ann. Rev. Biochem. 57:433-478 and contents (2 pages).
Yu et al. (2011) Understanding the intracellular effect of enhanced nutrient feeding toward high titer antibody production process. Biotechnol. & Bioengineer. 108(5):1078-1088.
Zogg et al. (2009) Structural basis of the cofactor- and substrate-assisted activation of human coagulation factor IXa. Structure. 17:1669-1678.

* cited by examiner

FIG. 5A

Neublastin antibody heavy chain (HC) with signal peptide (SEQ ID NO:1)

MDSRLNLVFLVLVLKGVLCEVKVVESGGGLVRPGGSLKLSCSASGFTFSSYAMSWVRQTPE
KRLEWVAYISHGGGDTYYLDTVKGRFTISRDNAKNSLYLQMSSLMSEDTAMYYCVRRGYD
YDGDYAMDYWGQGTSVTVSSAKTTPPSVYPLAPGSAAQTNSMVTLGCLVKGYFPEPVTVT
WNSGSLSSGVHTFPAVLQSDLYTLSSSVTVPSSTWPSETVTCNVAHPASSTKVDKKIVPRDCG
CKPCICTVPEVSSVFIFPPKPKDVLTITLTPKVTCVVVDISKDDPEVQFSWFVDDVEVHTAQTQ
PREEQFNSTFRSVSELPIMHQDWLNGKEFKCRVNSAAFPAPIEKTISKTKGRPKAPQVYTIPPP
KEQMAKDKVSLTCMITDFFPEDITVEWQWNGQPAENYKNTQPIMDTDGSYFVYSKLNVQKS
NWEAGNTFTCSVLHEGLHNHHTEKSLSHSPGK

FIG. 5B

Neublastin antibody heavy chain (HC), mature (no signal peptide) (SEQ ID NO:2)

EVKVVESGGGLVRPGGSLKLSCSASGFTFSSYAMSWVRQTPEKRLEWVAYISHGGGDTYYL
DTVKGRFTISRDNAKNSLYLQMSSLMSEDTAMYYCVRRGYDYDGDYAMDYWGQGTSVTV
SSAKTTPPSVYPLAPGSAAQTNSMVTLGCLVKGYFPEPVTVTWNSGSLSSGVHTFPAVLQSD
LYTLSSSVTVPSSTWPSETVTCNVAHPASSTKVDKKIVPRDCGCKPCICTVPEVSSVFIFPPKP
KDVLTITLTPKVTCVVVDISKDDPEVQFSWFVDDVEVHTAQTQPREEQFNSTFRSVSELPIMH
QDWLNGKEFKCRVNSAAFPAPIEKTISKTKGRPKAPQVYTIPPPKEQMAKDKVSLTCMITDFF
PEDITVEWQWNGQPAENYKNTQPIMDTDGSYFVYSKLNVQKSNWEAGNTFTCSVLHEGLH
NHHTEKSLSHSPGK

FIG. 5C

Neublastin antibody light chain (LC) with signal peptide (SEQ ID NO:3)

MKSQTQVFVFLLLCVSGAHGSIVMTQTPKFLLVSAGDRVTITCKASQSVSNAVAWFQQKPG
QSPKLLIYFASNRFTGVPDRFTGSGYGTDFTFTISTVQPEDLAVYFCQQDYNSPFTFGSGTKLE
IKRADAAPTVSIFPPSSEQLTSGGASVVCFLNNFYPRDINVKWKIDGSERQNGVLNSWTDQDS
KDSTYSMSSTLTLTKDEYERHNSYTCEATHKTSTSPIVKSFNRNEC

FIG. 5D

Neublastin antibody light chain (LC), mature (no signal peptide) (SEQ ID NO:4)

SIVMTQTPKFLLVSAGDRVTITCKASQSVSNAVAWFQQKPGQSPKLLIYFASNRFTGVPDRF
TGSGYGTDFTFTISTVQPEDLAVYFCQQDYNSPFTFGSGTKLEIKRADAAPTVSIFPPSSEQLT
SGGASVVCFLNNFYPRDINVKWKIDGSERQNGVLNSWTDQDSKDSTYSMSSTLTLTKDEYE
RHNSYTCEATHKTSTSPIVKSFNRNEC

FIG. 8A

Results for 465 residue sequence "HC with signal peptide" starting "MDSRLNLVFL"

>reverse translation to a 1395 base sequence of most likely codons.

atggatagccgcctgaacctggtgtttctggtgctggtgctgaaaggcgtgctgtgcgaa
gtgaaagtggtggaaagcggcggcggcctggtgcgcccgggcggcagcctgaaactgagc
tgcagcgcgagcggctttacctttagcagctatgcgatgagctgggtgcgccagaccccg
gaaaaacgcctggaatgggtggcgtatattagccatggcggcggcgatacctattatctg
gataccgtgaaaggccgctttaccattagccgcgataacgcgaaaaacagcctgtatctg
cagatgagcagcctgatgagcgaagataccgcgatgtattattgcgtgcgccgcggctat
gattatgatggcgattatgcgatggattattggggccagggcaccagcgtgaccgtgagc
agcgcgaaaaccaccccgccgagcgtgtatccgctggcgccgggcagcgcggcgcagacc
aacagcatggtgaccctgggctgcctggtgaaaggctatttttccggaaccggtgaccgtg
acctggaacagcggcagcctgagcagcggcgtgcatacctttccggcggtgctgcagagc
gatctgtataccctgagcagcagcgtgaccgtgccgagcagcacctggccgagcgaaacc
gtgacctgcaacgtggcgcatccggcgagcagcaccaaagtggataaaaaaattgtgccg
cgcgattgcggctgcaaaccgtgcatttgcaccgtgccggaagtgagcagcgtgtttatt
tttccgccgaaaccgaaagatgtgctgaccattaccctgaccccgaaagtgacctgcgtg
gtggtggatattagcaaagatgatccggaagtgcagtttagctggtttgtggatgatgtg
gaagtgcataccgcgcagacccagccgcgcgaagaacagtttaacagcacctttcgcagc
gtgagcgaactgccgattatgcatcaggattggctgaacggcaaagaatttaaatgccgc
gtgaacagcgcggcgtttccggcgccgattgaaaaaaccattagcaaaaccaaaggccgc
ccgaaagcgccgcaggtgtataccattccgccgccgaaagaacagatggcgaaagataaa
gtgagcctgacctgcatgattaccgatttttttccggaagatattaccgtggaatggcag
tggaacggccagccggcggaaaactataaaaacacccagccgattatggataccgatggc
agctattttgtgtatagcaaactgaacgtgcagaaaagcaactgggaagcgggcaacacc
tttacctgcagcgtgctgcatgaaggcctgcataaccatcataccgaaaaaagcctgagc
catagcccgggcaaa

FIG. 8B

>reverse translation to a 1395 base sequence of consensus codons.

atggaywsnmgnytnaayytngtnttyytngtnytngtnytnaarggngtnytntgygar
gtnaargtngtngarwsnggnggnggnytngtnmgnccnggnggnwsnytnaarytnwsn
tgywsngcnwsnggnttyacnttywsnwsntaygcnatgwsntgggtnmgncaracnccn
garaarmgnytngartgggtngcntayathwsncayggnggnggngayacntaytayytn
gayacngtnaarggnmgnttyacnathwsnmgngayaaygcnaaraaywsnytntayytn
caratgwsnwsnytnatgwsngargayacngcnatgtaytaytgygtnmgnmgnggntay
gaytaygayggngaytaygcnatggaytaytggggncarggnacnwsngtnacngtnwsn
wsngcnaaracnacnccnccnwsngtntayccnytngcnccnggnwsngcngcncaracn
aaywsnatggtnacnytnggntgyytngtnaarggntayttyccngarccngtnacngtn
acntggaaywsnggnwsnytnwsnwsnggngtncayacnttyccngcngtnytncarwsn
gayytntayacnytnwsnwsnwsngtnacngtnccnwsnwsnacntggccnwsngaracn
gtnacntgyaaygtngcncayccngcnwsnwsnacnaargtngayaaraarathgtnccn
mgngaytgyggntgyaarccntgyathtgyacngtnccngargtnwsnwsngtnttyath
ttyccnccnaarccnaargaygtnytnacnathacnytnacnccnaargtnacntgygtn
gtngtngayathwsnaargaygayccngargtncarttywsntggttygtngaygaygtn
gargtncayacngcncaracncarccnmgngargarcarttyaaywsnacnttymgnwsn
gtnwsngarytnccnathatgcaycargaytggytnaayggnaargarttyaartgymgn
gtnaaywsngcngcnttyccngcnccnathgaraaracnathwsnaaracnaarggnmgn
ccnaargcnccncargtntayacnathccnccnccnaargarcaratggcnaargayaar
gtnwsnytnacntgyatgathacngayttyttyccngargayathacngtngartggcar
tggaayggncarccngcngaraaytayaaraayacncarccnathatggayacngayggn
wsntayttygtntaywsnaarytnaaygtncaraarwsnaaytgggargcnggnaayacn
ttyacntgywsngtnytncaygarggnytncayaaycaycayacngaraarwsnytnwsn
caywsnccnggnaar

FIG. 8C

Results for 446 residue sequence " HC, mature (no signal peptide)" starting "EVKVVESGGG"

>reverse translation to a 1338 base sequence of most likely codons.

gaagtgaaagtggtggaaagcggcggcggcctggtgcgcccgggcggcagcctgaaactg
agctgcagcgcgagcggctttacctttagcagctatgcgatgagctgggtgcgccagacc
ccggaaaaacgcctggaatgggtggcgtatattagccatggcggcggcgatacctattat
ctggataccgtgaaaggccgctttaccattagccgcgataacgcgaaaaacagcctgtat
ctgcagatgagcagcctgatgagcgaagataccgcgatgtattattgcgtgcgccgcggc
tatgattatgatggcgattatgcgatggattattggggccagggcaccagcgtgaccgtg
agcagcgcgaaaaccaccccgccgagcgtgtatccgctggcgccgggcagcgcggcgcag
accaacagcatggtgaccctgggctgcctggtgaaaggctatttttccggaaccggtgacc
gtgacctggaacagcggcagcctgagcagcggcgtgcatacctttccggcggtgctgcag
agcgatctgtataccctgagcagcagcgtgaccgtgccgagcagcacctggccgagcgaa
accgtgacctgcaacgtggcgcatccggcgagcagcaccaaagtggataaaaaaattgtg
ccgcgcgattgcggctgcaaaccgtgcatttgcaccgtgccggaagtgagcagcgtgttt
atttttccgccgaaaccgaaagatgtgctgaccattaccctgaccccgaaagtgacctgc
gtggtggtggatattagcaaagatgatccggaagtgcagtttagctggtttgtggatgat
gtggaagtgcataccgcgcagacccagccgcgcgaagaacagtttaacagcacctttcgc
agcgtgagcgaactgccgattatgcatcaggattggctgaacggcaaagaatttaaatgc
cgcgtgaacagcgcggcgtttccggcgccgattgaaaaaaccattagcaaaaccaaaggc
cgcccgaaagcgccgcaggtgtataccattccgccgccgaaagaacagatggcgaaagat
aaagtgagcctgacctgcatgattaccgatttttttccggaagatattaccgtggaatgg
cagtggaacggccagccggcggaaaactataaaaacacccagccgattatggataccgat
ggcagctattttgtgtatagcaaactgaacgtgcagaaaagcaactgggaagcgggcaac
acctttacctgcagcgtgctgcatgaaggcctgcataaccatcataccgaaaaaagcctg
agccatagcccgggcaaa

FIG. 8D

>reverse translation to a 1338 base sequence of consensus codons.

gargtnaargtngtngarwsnggnggnggnytngtnmgnccnggnggnwsnytnaarytn
wsntgywsngcnwsnggnttyacnttywsnwsntaygcnatgwsntgggtnmgncaracn
ccngaraarmgnytngartgggtngcntayathwsncayggnggnggngayacntaytay
ytngayacngtnaarggnmgnttyacnathwsnmgngayaaygcnaaraaywsnytntay
ytncaratgwsnwsnytnatgwsngargayacngcnatgtaytaytgygtnmgnmgnggn
taygaytaygayggngaytaygcnatggaytaytggggncarggnacnwsngtnacngtn
wsnwsngcnaaracnacnccnccnwsngtntayccnytngcnccnggnwsngcngcncar
acnaaywsnatggtnacnytnggntgyytngtnaarggntayttyccngarccngtnacn
gtnacntggaaywsnggnwsnytnwsnwsnggngtncayacnttyccngcngtnytncar
wsngayytntayacnytnwsnwsnwsngtnacngtnccnwsnwsnacntggccnwsngar
acngtnacntgyaaygtngcncayccngcnwsnwsnacnaargtngayaaraarathgtn
ccnmgngaytgyggntgyaarccntgyathtgyacngtnccngargtnwsnwsngtntty
athttyccnccnaarccnaargaygtnytnacnathacnytnacnccnaargtnacntgy
gtngtngtngayathwsnaargaygayccngargtncarttywsntggttygtngaygay
gtngargtncayacngcncaracncarccnmgngargarcarttyaaywsnacnttymgn
wsngtnwsngarytnccnathatgcaycargaytggytnaayggnaargarttyaartgy
mgngtnaaywsngcngcnttyccngcnccnathgaraaracnathwsnaaracnaarggn
mgnccnaargcnccncargtntayacnathccnccnccnaargarcaratggcnaargay
aargtnwsnytnacntgyatgathacngayttyttyccngargayathacngtngartgg
cartggaayggncarccngcngaraaytayaaraayacncarccnathatggayacngay
ggnwsntayttygtntaywsnaarytnaaygtncaraarwsnaaytgggargcnggnaay
acnttyacntgywsngtnytncaygarggnytncayaaycaycayacngaraarwsnytn
wsncaywsnccnggnaar

FIG. 8E

Results for 234 residue sequence "LC with signal peptide" starting "MKSQTQVFVF"

>reverse translation of LC with signal peptide to a 702 base sequence of most likely codons.

atgaaaagccagacccaggtgtttgtgtttctgctgctgtgcgtgagcggcgcgcatggc
agcattgtgatgacccagaccccgaaatttctgctggtgagcgcgggcgatcgcgtgacc
attacctgcaaagcgagccagagcgtgagcaacgcggtggcgtggtttcagcagaaaccg
ggccagagcccgaaactgctgatttattttgcgagcaaccgctttaccggcgtgccggat
cgctttaccggcagcggctatggcaccgattttacctttaccattagcaccgtgcagccg
gaagatctggcggtgtattttgccagcaggattataacagcccgtttacctttggcagc
ggcaccaaactggaaattaaacgcgcggatgcggcgccgaccgtgagcattttttccgccg
agcagcgaacagctgaccagcggcggcgcgagcgtggtgtgctttctgaacaacttttat
ccgcgcgatattaacgtgaaatggaaaattgatggcagcgaacgccagaacggcgtgctg
aacagctggaccgatcaggatagcaaagatagcacctatagcatgagcagcaccctgacc
ctgaccaaagatgaatatgaacgccataacagctatacctgcgaagcgacccataaaacc
agcaccagcccgattgtgaaaagctttaaccgcaacgaatgc

FIG. 8F

>reverse translation of LC with signal peptide to a 702 base sequence of consensus codons.

atgaarwsncaracncargtnttygtnttyytnytnytntgygtnwsnggngcncayggn
wsnathgtnatgacncaracnccnaarttyytnytngtnwsngcnggngaymgngtnacn
athacntgyaargcnwsncarwsngtnwsnaaygcngtngcntggttycarcaraarccn
ggncarwsnccnaarytnytnathtayttygcnwsnaaymgnttyacnggngtnccngay
mgnttyacnggnwsnggntayggnacngayttyacnttyacnathwsnacngtncarccn
gargayytngcngtntayttytgycarcargaytayaaywsnccnttyacnttyggnwsn
ggnacnaarytngarathaarmgngcngaygcngcnccnacngtnwsnathttyccnccn
wsnwsngarcarytnacnwsnggnggngcnwsngtngtntgyttyytnaayaayttytay
ccnmgngayathaaygtnaartggaarathgayggnwsngarmgncaraayggngtnytn
aaywsntggacngaycargaywsnaargaywsnacntaywsnatgwsnwsnacnytnacn
ytnacnaargaygartaygarmgncayaaywsntayacntgygargcnacncayaaracn
wsnacnwsnccnathgtnaarwsnttyaaymgnaaygartgy

FIG. 8G

Results for 214 residue sequence "LC, mature (no signal peptide):" starting "SIVMTQTPKF"

>reverse translation of LC, mature (no signal peptide): to a 642 base sequence of most likely codons.

```
agcattgtgatgacccagaccccgaaatttctgctggtgagcgcgggcgatcgcgtgacc
attacctgcaaagcgagccagagcgtgagcaacgcggtggcgtggtttcagcagaaaccg
ggccagagcccgaaactgctgatttattttgcgagcaaccgctttaccggcgtgccggat
cgctttaccggcagcggctatggcaccgattttacctttaccattagcaccgtgcagccg
gaagatctggcggtgtatttttgccagcaggattataacagcccgtttacctttggcagc
ggcaccaaactggaaattaaacgcgcggatgcggcgccgaccgtgagcattttccgccg
agcagcgaacagctgaccagcggcggcgcgagcgtggtgtgctttctgaacaacttttat
ccgcgcgatattaacgtgaaatggaaaattgatggcagcgaacgccagaacggcgtgctg
aacagctggaccgatcaggatagcaaagatagcacctatagcatgagcagcaccctgacc
ctgaccaaagatgaatatgaacgccataacagctatacctgcgaagcgacccataaaacc
agcaccagcccgattgtgaaaagctttaaccgcaacgaatgc
```

FIG. 8H

>reverse translation of LC, mature (no signal peptide): to a 642 base sequence of consensus codons.

```
wsnathgtnatgacncaracnccnaarttyytnytngtnwsngcnggngaymgngtnacn
athacntgyaargcnwsncarwsngtnwsnaaygcngtngcntggttycarcaraarccn
ggncarwsnccnaarytnytnathtayttygcnwsnaaymgnttyacnggngtnccngay
mgnttyacnggnwsnggntayggnacngayttyacnttyacnathwsnacngtncarccn
gargayytngcngtntayttytgycarcargaytayaaywsnccnttyacnttyggnwsn
ggnacnaarytngarathaarmgngcngaygcngcnccnacngtnwsnathttyccnccn
wsnwsngarcarytnacnwsnggnggngcnwsngtngtntgyttyytnaayaayttytay
ccnmgngayathaaygtnaartggaarathgayggnwsngarmgncaraayggngtnytn
aaywsntggacngaycargaywsnaargaywsnacntaywsnatgwsnwsnacnytnacn
ytnacnaargaygartaygarmgncayaaywsntayacntgygargcnacncayaaracn
wsnacnwsnccnathgtnaarwsnttyaaymgnaaygartgy
```

MAMMALIAN CELL CULTURE-PRODUCED NEUBLASTIN ANTIBODIES

This application is a continuation-in-part of U.S. application Ser. No. 15/291,257 filed Oct. 12, 2016, which is a continuation of U.S. application Ser. No. 14/760,182 filed Jul. 9, 2015, which is a 35 U.S.C. 371 national stage application of PCT/US14/11130 filed Jan. 10, 2014, which claims the benefit of U.S. provisional application No. 61/751,067 filed Jan. 10, 2013, the disclosures of which are hereby incorporated by reference in their entirety.

FIELD OF THE INVENTION

The present invention pertains to a cell culture medium comprising dextran sulfate or a mixture of dextran sulfate and ferric citrate, and methods of use. The present invention further pertains to a method of producing a protein of interest in a large-scale cell culture, a method of producing neublastin antibodies in mammalian cells, and to neublastin antibodies produced in mammalian cell culture.

BACKGROUND

Over the last few decades, much research has focused on the production of recombinant proteins, e.g. monoclonal antibodies, and the work has taken a variety of angles. While much work in the literature has utilized media containing sera or hydrolysates, chemically defined media were also developed in order to eliminate the problematic lot-to-lot variation of complex components (Luo and Chen, *Biotechnol. Bioeng.* 97(6):1654-165.9 (2007)). An improved understanding of the cell culture has permitted a shift to chemically defined medium without compromising on growth, viability, titer, etc., To date optimized chemically defined processes have been reported with titers as high as 7.5-10 g/L (Huang et al., Biotechnology Progress 26(5):1400-1410 (2010); Ma et at, *Biotechnol. Prog.* 25(5):1353-1363 (2009); Yu et al.; *Biotechnol. Bioeng.* 108(5):1078-1088 (2011)). In general, the high titer chemically defined processes are fed batch processes with cultivation times of 11-18 days. The process intensification has been achieved without compromising product quality while maintaining relatively high viabilities.

Achievement of a robust, scalable production process includes more than increasing the product titer while maintaining high product quality. The process must also predictably require the main carbohydrate source such that the feeding strategy does not need to change across scales. As many processes use glucose as the main carbohydrate, and have lactate and ammonium as the main byproducts, the time course of these three critical chemicals should also scale.

A recent metabolomics study performed by Ma and coworkers (Ma et al., *Biotechnol. Prog.* 25(5):1353-1363 (2009)) suggested a blockage in the TCA cycle, resulting in an early phase secretion of citrate and later citrate consumption. The process used by Ma may also have subsequently resulted in high LPR: if the viability permitted further extension of the process. The feeding of pyruvate (0.02 M) was shown to increase antibody production by 43% in a continuous culture of a hybridoma cell (Omasa et al., *Bioproc. Biosys. Engin.* 33(1):117-125 (2010)). The feeding of citrate (0.05 M and 0.01 M) in the same culture system resulted only in a ~5-10% increase in antibody production. Bai recently reported increased antibody production in a chemically defined CHO cell culture supplemented with a combination of high concentrations of chemically defined iron and high concentrations of citrate (Bai et al., *Biotechnol. Prog.* 27(1):209-219 (2011)). Citrate supplementation alone, however, could not support stable cell growth at all.

There is a need in the art to further improve recombinant protein production processes to eliminate lot-to-lot metabolic variability. Provided herein are compositions and methods to prevent or reduce metabolic variability encountered in recombinant protein producing cell cultures.

SUMMARY OF THE INVENTION

The present invention pertains to a method of culturing cells in a medium comprising supplementing the medium with a feed comprising a sufficient amount of dextran sulfate. The present invention also pertains to a method of culturing cells in a medium comprising or supplementing the medium with a feed comprising a mixture of dextran sulfate and ferric citrate.

In one embodiment, the medium and/or feed comprise dextran sulfate in an amount sufficient to increase the dextran sulfate concentration in the medium by between about 0.1 g/L and about 5 g/L. In another embodiment, the medium and/or feed comprise ferric citrate in an amount sufficient to raise the ferric citrate concentration in the medium about 1 mM and about 50 mM.

The present invention also pertains to a cell culture medium comprising dextran sulfate or a mixture of dextran sulfate and ferric citrate.

The present invention further provides a cell culture composition comprising cells capable of expressing a polypeptide of interest and a medium comprising dextran sulfate or a mixture of dextran sulfate and ferric citrate.

The present invention further pertains to a conditioned cell culture medium produced by a method disclosed herein. In one embodiment, the conditioned medium comprises a polypeptide of interest produced by a method disclosed herein. In a specific embodiment, a conditioned medium according to the present invention comprises an antibody. In another specific embodiment, a conditioned medium according to the present invention comprises a Transforming Growth Factor (TGF) beta superfamily signaling molecule. In yet another specific embodiment, a conditioned medium according to the present invention comprises a blood clotting factor.

In still another aspect, the disclosure provides a cell culture comprising a mammalian cell line that has been genetically modified to express a neublastin antibody polypeptide, or a fragment thereof, in the cell culture medium. In certain embodiments, the mammalian cell line is a Chinese Hamster Ovary (CHO) cell line. In some embodiments, the neublastin antibody polypeptide, or fragment thereof, comprises SEQ ID NO:2, or a portion thereof, and/or SEQ ID NO:4, or a portiont thereof. In particular embodiments, the cells have been adapted to grow in a serum-free medium, an animal protein-free medium, or a chemically defined medium.

In some embodiments, the mammalian cell culture is a perfusion culture or is a fed batch culture. In certain embodiments, the cell culture medium is a serum-free medium, an animal protein-free medium, or a chemically defined medium.

In yet another aspect, the disclosure provides a neublastin antibody polypeptide, or fragment thereof, produced in a mammalian cell culture, the culture comprising mammalian cells genetically modified to express, and which express, the neublastin antibody polypeptide, or a fragment thereto, in the mammalian cell culture. In some embodiments, the mammalian cell line is a CHO cell line. In some embodiments, the neublastin antibody polypeptide, or fragment thereof, comprises SEQ ID NO:2, or a portion thereof, and/or SEQ ID NO:4, or a portion thereof. In particular embodiments, the cells have been adapted to grow in serum-free medium, an animal protein-free medium, or a chemically defined medium. In some embodiments, the neublastin antibody polypeptide, or fragment thereof, has been isolated from the mammalian cell culture.

In another aspect, the disclosure provides a pharmaceutical formulation comprising a neublastin antibody polypeptide, or fragment thereof, which has been isolated from a mammalian cell culture comprising mammalian cells genetically modified to express the neublastin antibody polypeptide, or a fragment thereto, in the mammalian cell culture. In some embodiments, the mammalian cell culture is a CHO cell culture. In particular embodiments, the neublastin antibody polypeptide comprises SEQ ID NO:2, or portion thereof, and/or SEQ ID NO:4, or a portion thereof.

BRIEF DESCRIPTION OF THE DRAWING

The foregoing and other objects of the present disclosure, the various features thereof, as well as the disclosure itself may be more fully understood from the following description, when read together with the accompanying drawings in which:

FIG. 5A is a schematic representation of the amino acid sequence of the heavy chain of the neublastin antibody including a signal peptide;

FIG. 5B is a schematic representation of the amino acid sequence of the heavy chain of the neublastin antibody;

FIG. 5C is a schematic representation of the amino acid sequence of the light chain of the neublastin antibody including a signal peptide;

FIG. 5D is a schematic representation of the amino acid sequence of the light chain of the neublastin antibody;

FIG. 8A is a schematic representation (SEQ ID NO: 5) of the neublastin heavy chain with signal peptide starting "MDSRLNLVFL" (residues 1 to 10 of SEQ ID NO: 1);

FIG. 8B is a schematic representation (SEQ ID NO: 6) of the degenerate reverse translation of the neublastin heavy chain;

FIG. 8C is a schematic representation (SEQ ID NO: 7) of the reverse translation of the neublastin heavy chain with no signal peptide starting "EVKVVESGGG" (residues 1 to 10 of SEQ ID NO: 2) showing the most likely codons;

FIG. 8D is a schematic representation (SEQ ID NO: 8) of the degenerate reverse translation of the neublastin heavy chain;

FIG. 8E is a schematic representation (SEQ ID NO: 9) of the reverse translation of the neublastin light chain with the signal peptide starting "MKSQTQVFVF" (residues 1 to 10 of SEQ ID NO: 3);

FIG. 8F is a schematic representation (SEQ ID NO: 10) of the degenerate reverse translation of the neublastin light chain;

FIG. 8G is a schematic representation (SEQ ID NO: 11) of the reverse translation of the neublastin light chain starting "SIVMTQTPKF" (residues 1 to 10 of SEQ ID NO: 4) showing the most likely codons; and FIG. 8H is a schematic representation (SEQ ID NO: 12) of the degenerate reverse translation of the neublastin light chain.

DETAILED DESCRIPTION

Figure 1A:
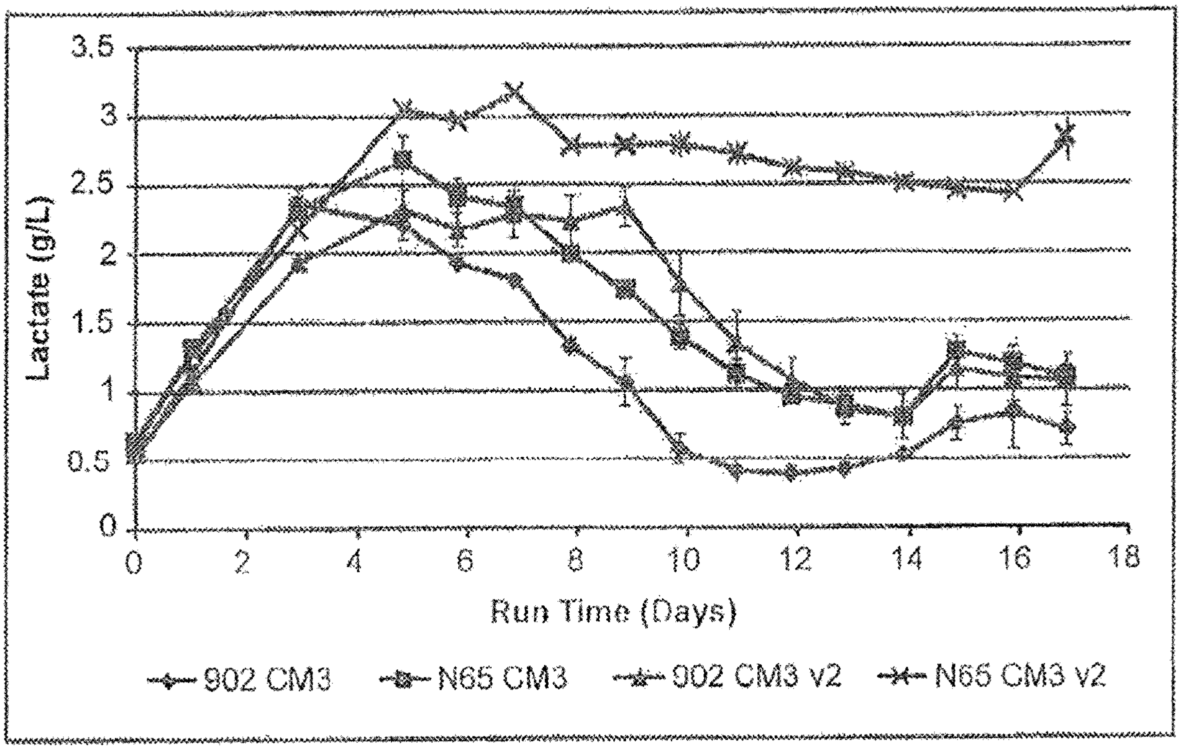
FIGS. 1A-1B are graphic representations of the citrate (A) and ammonium production (B) after addition of ferric citrate and dextran sulfate maintains lactate levels and decreases ammonium production.

All documents, articles, publications, patents, and patent applications mentioned in this specification are herein incorporated by reference to the same extent as if each individual publication or patent application was specifically and individually indicated to be incorporated by reference.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

I. Definitions

The term "antibody" is used to mean an immunoglobulin molecule that recognizes and specifically binds to a target or antigen, such as a protein, polypeptide, peptide, carbohydrate, polynucleotide, lipid, or combinations of the foregoing etc., through at least one antigen recognition site within the variable region of the immunoglobulin molecule. As used, herein, the term encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

The term "basal media formulation" or "basal media" as used herein refers to any cell culture media used to culture cells that has not been modified either by supplementation, or by selective removal of a certain component.

The term "batch culture" as used herein refers to a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

The term "bioreactor" as used herein refers to any vessel used for the growth of a mammalian cell culture. The bioreactor can be of any size so long as it is useful for the culturing of mammalian cells. Typically, the bioreactor will be at least 1 titer and can be 10, 50, 100, 250, 500, 1000, 2000, 2,500, 3000, 5000, 8000, 10,000, 12,000, 15,000, 20,000, 30,000 liters or more, or any volume in between. For example, a bioreactor will be 10 to 5,000 liters, 10 to 10,000 liters, 10 to 15,000 liters, 10 to 20,000 liters, 10 to 30,000 liters, 50 to 5,000 liters, 50 to 10,000 liters, 50 to 15,000 liters, 50 to 20,000 liters, 50 to 30,000 liters, 1,000 to 5,000 liters, or 1,000 to 3,000 liters. The internal conditions of the bioreactor, including, but not limited to pH and temperature, are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or protein of interest. The volume of the large-scale cell culture production bioreactor is typically at least 500 liters and can be 1000, 2000, 2500, 5000, 8000, 10,000, 12,0000, 15,000 liters or more, or any volume in between. For example, the large scale cell culture reactor will be between about 500 liters and about 20,000 liters, about 500 liters and about 10,000 liters, about 500 liters and about 5,000 liters, about 1,000 liters and about 30,000 liters, about 2,000 liters and about 30,000 liters, about 3,000 liters and about 30,000 liters, about 5,000 liters and about 30,000 liters, or about 10,000 liters and about 30,000 liters, or a large scale cell culture reactor will be at least about 500 liters, at least about 1,000 liters, at least about 2,000 liters, at least about 3,000 liters, at least about 5,000 liters, at least about 10,000 liters; at least about 15,000 liters, or at least about 20,000 liters. One of ordinary skill in the art will be aware of and will be able to choose suitable bioreactors for use in practicing, the present invention.

The term "cell density" as used herein refers to that number of cells present in a given volume of medium.

The terms "culture", "cell culture", and "eukaryotic cell culture" as used herein refer to a eukaryotic cell population that is suspended in a medium (see definition of "medium" below) under conditions suitable to survival and/or growth of the cell population. As will be clear to those of ordinary skill in the art, these terms as used herein can refer to the combination comprising the mammalian cell population and the medium in which the population is suspended.

The term "fed-batch culture" as used herein refers to a method of culturing cells in which additional components are provided to the culture at some time subsequent to the beginning of the culture process. A fed-batch culture can be started using a basal medium. The culture medium with which additional components are provided to the culture at some time subsequent to the beginning of the culture process is a feed medium. The provided components typically comprise nutritional supplements for the cells which have been depleted during the culturing process. In one embodiment, a feed medium described herein comprises dextran sulfate or a mixture of dextran sulfate and ferric citrate. In another embodiment, a feed medium described herein consists of dextran sulfate or a mixture of dextran sulfate and ferric citrate. A fed-batch culture is typically stopped at some point and the cells and/or components in the medium are harvested and optionally purified.

"Growth phase" of the cell culture refers to the period of exponential cell growth (the log phase) where cells are generally rapidly dividing. During this phase, cells are cultured for a period, usually between 1-4 days, and under such conditions that cell growth is maximized. The determination of the growth cycle for the host cell can be determined for the host cell envisioned without undue experimentation. "Period of time and under such conditions that cell growth is maximized" and the like, refer to those culture conditions that, for a cell line, are determined to be optimal for cell growth and division. During the growth phase, cells are cultured in nutrient medium containing the necessary additives generally at about 25°-40° C., in a humidified, controlled atmosphere, such that optimal growth is achieved for the cell line. Cells are maintained in the growth phase for a period of about between one and four days, usually between two to three days. The length of the growth phase for the cells can be determined without undue experimentation. For example, the length of the growth phase will be the period of time sufficient to allow the particular cells to reproduce to a viable cell density within a range of about 20%-80% of the maximal possible viable cell density if the culture was maintained under the growth conditions.

"Production phase" of the cell culture refers to the period of time during which cell growth has plateaued. During the production phase, logarithmic cell growth has ended and protein production is primary. During this period of time the medium is generally supplemented to support continued protein production and to achieve the desired glycoprotein product.

The term "expression" or "expresses" are used herein to refer to transcription and translation occurring within a host cell. The level of expression of a product gene in a host cell can be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook et al., *Molecular Cloning: A Laboratory Manual*, pp. 7.3-7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein. Sambrook et al., *Molecular Cloning: A Laboratory Manual*, pp. 18.1-18.88 (Cold Spring Harbor Laboratory Press, 1989).

The term "hybridoma" as used herein refers to a cell created by fusion of an immortalized cell derived from an immunologic source and an antibody-producing cell. The resulting hybridoma is an immortalized cell that produces antibodies. The individual cells used to create the hybridoma can be from any mammalian source, including, but not limited to, rat, pig, rabbit, sheep, pig, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., *Nature,* 537:3053 (1983).

The terms "medium", "cell culture medium", "culture medium", and "growth medium" as used herein refer to a solution containing nutrients which nourish growing eukaryotic cells. Typically, these solutions provide essential and non-essential amino acids, vitamins, energy sources, lipids, and trace elements required by the cell for minimal growth and/or survival. The solution can also contain components that enhance growth and/or survival above the minimal rate, including hormones and growth factors. The solution is formulated to a pH and salt concentration optimal for cell survival and proliferation. The medium can also be a "defined medium" or "chemically defined medium" a serum-free medium that contains no proteins, hydrolysates or components of unknown composition. Defined media are free of animal-derived components and all components have a known chemical structure. One of skill in the art understands a defined medium can comprise recombinant polypeptides or proteins, for example, but not limited to, hormones, cytokines, interleukins and other signaling molecules.

The term "perfusion culture" as used herein refers to a method of culturing cells in which additional components are provided continuously or semi-continuously to the culture subsequent to the beginning of the culture process. The provided components-typically comprise nutritional supplements for the cells which have been depleted during the culturing process. A portion of the cells and/or components in the medium are typically harvested on a continuous or semi-continuous basis and are optionally purified.

The terms "polypeptide" or "protein" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit, the terms "polypeptide" and "protein" as used herein are used interchangeably. If discrete functional unit is comprised of more than one polypeptide that physically associate with one another, the term "protein" as used herein refers to the multiple polypeptides that are physically coupled and function together as the discrete unit.

"Recombinantly expressed polypeptide" and "recombinant polypeptide" as used herein refer to a polypeptide expressed from a host cell that has been genetically engineered to express that polypeptide. The recombinantly expressed polypeptide can be identical or similar to polypeptides that are normally expressed in the mammalian host cell. The recombinantly expressed polypeptide can also foreign to the host cell, i.e. heterologous to peptides normally expressed in the mammalian host cell. Alternatively, the recombinantly expressed polypeptide can be chimeric in that portions of the polypeptide that contain amino acid sequences that are identical or similar to polypeptides normally expressed in the mammalian host cell, while other portions are foreign to the host cell. As used herein, the terms "recombinantly expressed polypeptide" and "recombinant polypeptide" also encompasses an antibody produced by a hybridoma.

The term "seeding" as used herein refers to the process of providing a cell culture to a bioreactor or another vessel. In one embodiment, the cells have been propagated previously in another bioreactor or vessel. In another embodiment, the cells have been frozen and thawed immediately prior to providing them to the bioreactor or vessel. The term refers to any number of cells, including a single cell.

The term "titer" as used herein refers to the total amount of recombinantly expressed polypeptide or protein produced by a cell culture divided by a given amount of medium volume. Titer is typically expressed in units of milligrams of polypeptide or protein per milliliter of medium or in units of grams of polypeptide or protein per liter of medium.

As used in the present disclosure and claims, the singular forms "a", "an", and "the" include plural forms unless the context clearly dictates otherwise.

It is understood that whenever embodiments are described herein with the language "comprising" otherwise analogous embodiments described in terms of "consisting" and/or "consisting essentially of" are also provided.

II. Cell Culture Medium and Methods of Using the Same

The present invention relates to cell culture media and methods of use thereof. The media of the invention reduces lot-to-lot metabolic variability associated with a metabolic shift to lactate production. A medium according to the invention can be used in a batch culture, fed-batch culture or a perfusion culture. In one embodiment, a medium of the invention is a basal medium. In another embodiment, a medium of the invention is a feed medium.

In one embodiment, a medium according to the present invention comprises dextran sulfate. A medium can comprise sufficient amount of dextran sulfate to increase the dextran sulfate concentration in the culture by between about 0.01 g/L and about 5 g/L. In one embodiment, a feed medium described herein comprises sufficient amount of dextran sulfate to increase the dextran sulfate concentration in the culture by between about 0.01 g/L and about 5 g/L, about 0.01 g/L and about 4 g/L, about 0.01 g/L and about 3 g/L, about 0.01 g/L and about 2 g/L, about 0.01 g/L and about 1 g/L, about 0.01 g/L and about 0.5 g/L, about 0.01 g/L and about 0.25 g/L, about 0.05 g/L and about 5 g/L, about 0.05 g/L and about 4 g/L, about 0.05 g/L and about 3 g/L, about 0.05 g/L and about 2 g/L, about 0.05 g/L and about 1 g/L, about 0.05 g/L and about 0.5 g/L, about 0.05 g/L and about 0.25 g/L, about 0.1 g/L and about 5 g/L, about 0.1 g/L and about 4 g/L, about 0.1 g/L and about 3 g/L, about 0.1 g/L and about 2 g/L, about 0.1 g/L and about 1 g/L, about 0.1 g/L and about 0.5 g/L, about 0.1 g/L and about 0.25 g/L, about 0.2 g/L and about 5 g/L, about 0.2 g/L and about 4 g/L, about 0.2 g/L, and about 3 g/L, about 0.2 g/L, and about 2 g/L, about 0.2 g/L and about 1 g/L, about 0.2 g/L and about 0.5 g/L, about 0.2 g/L and about 0.25 g/L, about 0.25 g/L and about 5 g/L, about 0.25 g/L and about 4 g/L, about 0.25 g/L and about 3 g/L, about 0.25 g/L and about 2 g/L, about 0.25 g/L and about 1 g/L, or about 0.25 g/L and about 0.5 g/L. In another embodiment, a feed medium described herein comprises sufficient amount of dextran sulfate to increase the dextran sulfate concentration in the culture by about 0.01 g/L, about 0.02 g/L, about 0.03 g/L, about 0.04 g/L, about 0.05 g/L, about 0.06 g/L, about 0.07 g/L, about 0.08 g/L, about 0.09 g/L, about 0.1 g/L, about 0.15 g/L, about 0.2 g/L, about 0.25 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, or about 5 g/L. A skilled artisan readily understands that the absolute amount of dextran sulfate supplemented by a feed medium to a cell culture can be calculated from the volume of feed medium added to the culture and the dextran sulfate concentration of the feed medium.

In one embodiment, a medium according to the present invention comprises a mixture of dextran sulfate and ferric citrate. A medium can comprise sufficient amount of ferric citrate to increase the ferric citrate concentration in the culture by between about 1 mM and about 50 mM. In one embodiment, a feed medium described herein comprises sufficient amount of ferric citrate to increase the ferric citrate concentration in the culture by between about 1 mM and about 50 mM, about 1 mM and about 40 mM, about 1 mM and about 35 mM, about 1 mM and about 30 mM, about 1 mM and about 25 mM, about 1 mM and about 20 mM, about 1 mM and about 15 mM, about 1 mM and about 14 mM, about 1 mM and about 13 mM, about 1 mM and about 12 mM, about 1 mM and about 11 mM, about 1 mM and about 10 mM, about 2 mM and about 50 mM, about 3 mM and about 50 mM, about 4 mM and about 50 mM, about 5 mM and about 50 mM, about 10 mM and about 50 mM, about 15 mM and about 50 mM, about 20 mM and about 50 mM, or about 30 mM and about 50 mM. In another embodiment, a feed medium described herein comprises sufficient amount of ferric citrate to increase the ferric citrate concentration in the culture by about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 30 mM, about 35 mM, about 40, about 45 mM or about 50 mM. A skilled artisan readily understands that the absolute amount of ferric citrate supplemented by a feed medium to a cell culture can be calculated from the volume of feed medium added to the culture and the ferric citrate concentration of the feed medium.

In one embodiment, a medium described herein is a serum-free medium, animal protein-free medium or a chemically-defined medium. In a specific embodiment, a medium described herein is a chemically-defined medium.

The present invention further provides a cell culture composition comprising a medium described herein and cells.

In one embodiment, a cell culture composition according to the invention can be a batch culture, fed-batch culture or a perfusion culture. In a specific embodiment, a cell culture composition of the invention is a fed batch culture.

In one embodiment, a cell culture composition described herein comprises mammalian cells such as, but not limited to, CHO cells, HEK cells, NSO cells, PER.C6 cells, 293 cells, HeLa cells, and MDCK cells. In a specific embodiment, a cell culture composition described herein comprises CHO cells. In another specific embodiment, a cell culture composition described herein comprises HEK cells. In another specific embodiment, a-cell culture composition described herein comprises hybridoma cells.

A cell culture composition described herein can comprise cells that have been adapted to grow in serum free medium, animal protein free medium or chemically defined medium. Alternatively, it can comprise cells that have been genetically modified to increase their life-span in culture. In one embodiment, the cells have been modified to express an anti-apoptotic gene. In a specific embodiment, the cells have been modified to express the bcl-xL antiapoptotic gene. Additional anti-apoptotic genes that can be used in accordance with the present invention include, but are not limited to, E1B-9K, Aven, Mc1.

The disclosure also provides, in another embodiment, a cell culture composition comprises mammalian cells adapted to produce neublastin antibodies, or fragments thereof. Also provided are useful cells for this purpose include, but are limited to, CHO cells, and retinal-derived cells, and neublastin antibodies, or fragments thereof, made in mammalian cells.

The present invention provides a method of culturing cells, comprising contacting the cells with a medium disclosed herein.

Cell cultures can be cultured in a batch culture, fed batch culture or a perfusion culture. In one embodiment, a cell culture according to a method of the present invention is a batch culture. In another embodiment, a cell culture according to a method of the present invention is a fed batch culture. In a further embodiment, a cell culture according to a method of the present invention is a perfusion culture.

In one embodiment, a cell culture according to a method of the present invention is a serum-free culture. In another embodiment, a cell culture according to a method of the present invention is a chemically defined culture. In a further embodiment, a cell culture according to a method of the present invention is an animal protein free culture.

In one embodiment, a cell culture is contacted with a medium described herein during the growth phase of the culture. In another embodiment, a cell culture is contacted with a medium described herein during the production phase of the culture.

In one embodiment, a cell culture according to the invention is contacted with a feed medium described herein during the production phase of the culture. In one embodiment, the culture is supplemented with the feed medium between about 1 and about 25 times during the second time period. In another embodiment, a culture is supplemented with the feed medium between about 1 and about 20 times, between about 1 and about 15 times, or between about 1 and about 10 times during the first time period. In a further embodiment, a culture is supplemented with the feed medium at least once, at least twice, at least three times, at least four times, at least five times, at least 6 times, at least 7 times, at least 8 times, at least 9 times, at least 10 times, at least 1 times, at least 12 times, at least 13 times, at least 14 times, at least 15 times, at least 20 times, at least 25 times. In a specific embodiment, the culture is a fed batch culture. In another specific embodiment, the culture is a perfusion culture.

A culture according to the invention can be contacted with a feed medium described herein at regular intervals. In one embodiment, the regular interval is about once a day, about once every two days, about once every three days, about once every 4 days, or about once every 5 days. In a specific embodiment, the culture is a fed hatch culture. In another specific embodiment, the culture is a perfusion culture.

A culture according to the invention can be contacted with a feed medium described herein on an as needed basis based on the metabolic status of the culture. In one embodiment, a metabolic marker of a fed hatch culture is measured prior to supplementing the culture with a feed medium described herein. In one embodiment, the metabolic marker is selected from the group consisting of: lactate concentration, ammonium concentration, alanine concentration, glutamine concentration, glutamate concentration, cell specific lactate production rate to the cell specific glucose uptake rate ratio (LPR/GUR ratio), and Khodarnine 123 specific cell fluorescence. In one embodiment, an LPR/GUR value of >0.1 indicates the need to supplement the culture with a feed medium described herein. In a further specific embodiment, a lactate concentration of >3 g/L indicates the need to supplement the culture with a feed medium described herein. In another embodiment, a culture according to the present invention is supplemented with a feed medium described herein when the LPR/GUR value of the culture is >0.1 or when the lactate concentration of the culture is >3 g/L. In a specific embodiment, the culture is a fed batch culture. In another specific embodiment, the culture is a perfusion culture.

In one embodiment, a medium described herein is a feed medium for a fed batch cell culture. A skilled artisan understands that a fed batch cell culture can be contacted with a feed medium more than once. In one embodiment, a fed batch cell culture is contacted with a medium described herein only once. In another embodiment, a fed batch cell culture is contacted with a medium described herein more than once, for example, at least twice, at least three times, at least four times, at least five times, at least six times, at least seven times, or at least ten times.

In accordance with the present invention, the total volume of feed medium added to a cell culture should optimally be kept to a minimal amount. For example, the total volume of the feed medium added to the cell culture can be 1, 2, 3, 4, 5, 6, 7, 8, 9, 10, 15, 20, 25, 30, 35, 40, 45 or 50% of the volume of the cell culture prior to adding the feed medium.

Cell cultures can be grown to achieve a particular cell density, depending on the needs of the practitioner and the requirement of the cells themselves, prior to being contacted with a medium described herein. In one embodiment, the cell culture is contacted with a medium described herein at a viable cell density of 1, 5, 10, 15, 20, 25, 30, 35, 40, 45, 50, 55, 60, 65, 70, 75, 80, 85, 90, 95 or 99 percent of maximal viable cell density. In a specific embodiment, the medium is a feed medium.

Cell cultures can be allowed to grow for a defined period of time before they are contacted with a medium described herein. In one embodiment, the cell culture is contacted with a medium described herein at day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the cell culture. In another embodiment, the cell culture is contacted with a medium described herein at week 1, 2, 3, 4, 5, 6, 7, or 8 of the cell culture. In a specific embodiment, the medium is a feed medium.

Cell cultures can be cultured in the production phase for a defined period of time. In one embodiment, the cell culture is contacted with a feed medium described herein at day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the production phase.

A culture according to the invention can be maintained in production phase for between about 1 day and about 30 days. In one embodiment, a culture is maintained in production phase for between about 1 day and about 30 days, between about 1 day and about 25 days, between about 1 day and about 20 days, about 1 day and about 15 days, about 1 day and about 14 days, about 1 day and about 13 days, about 1 day and about 12 days, about 1 day and about 11 days, about 1 day and about 10 days, about 1 day and about 9 days, about 1 day and about 8 days, about 1 day and about 7 days, about 1 day and about 6 days, about 1 day and about 5 days, about 1 day and about 4 days, about 1 day and about 3 days, about 2 days and about 25 days, about 3 days and about 25 days, about 4 days and about 25 days, about 5 days and about 25 days, about 6 days and about 25 days, about 7 days and about 25 days, about 8 days and about 25 days, about 9 days and about 25 days, about 10 days and about 25 days, about 15 days and about 25 days, about 20 days and about 25 days, about 2 days and about 30 days, about 3 days and about 30 days, about 4 days and about 30 days, about 5 days and about 30 days, about 6 days and about 30 days, about 7 days and about 30 days, about 8 days and about 30 days, about 9 days and about 30 days, about 10 days and about 30 days, about 15 days and about 30 days, about 20 days and about 30 days, or about 25 days and about 30 days. In another embodiment, a culture is maintained in production phase for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 15 days, at least about 20 days, at least about 25 days, or at least about 30 days. In a further embodiment, a culture is maintained in production phase for about 1 day, about 2 days, about 3 days, about 4 days, about 5 days, about 6 days, about 7 days, about 8 days, about 9 days, about 10 days, about 11 days, about 12 days, about 15 days, about 20 days, about 25 days, or about 30 days.

The present invention further provides a method of preventing or reducing metabolic imbalance in a cell culture. Metabolic imbalance can be monitored by measuring the levels of metabolites in the cell culture. For example, metabolic imbalance can be detected by monitoring lactate production, ammonium production, the ratio of cell specific lactate production rate (LPR) to cell specific glucose uptake rate (GUR), alanine consumption, or glutamine consumption in a cell culture. In one embodiment, metabolic imbalance is signaled by increased lactate production, increased ammonium production or an increase in the cell specific lactate production rate to cell specific glucose uptake rate ratio ("LPR/GUR ratio"). In another embodiment, metabolic imbalance is signaled by an increase in alanine consumption or by an increase in glutamine consumption.

In one embodiment, a method of culturing cells according to the present invention prevents or reduces mitochondria dysfunction or metabolic imbalance during the exponential growth phase. In another embodiment, a method of culturing cells according to the present invention prevents or reduces mitochondria dysfunction or metabolic imbalance after the cells passed the exponential growth phase. In a further embodiment, a method of culturing cells—according to the present invention prevents or reduces mitochondrial dysfunction or metabolic imbalance during the production phase.

The present invention also provides a method of decreasing lactate production by a cell culture, comprising contacting the cell culture with a medium described herein. In one embodiment, the lactate production of cells maintained in a culture medium described herein is between about 5% and about 90%, between about S %, and about 80%, between about 5%, and about 70%, between about 5%, and about 50%, between about 5%, and about 40%, between about 5%, and about 30%, between about 5%, and about 20%, between about 10%, and about 90%, between about 20%, and about 90%, between about 30%, and about 90%, or between about 50%, and about 90%, or at least about 5%, at least about 10%, at least about 20%, at least about 30%, at least about 50%, or at least about 90%, or about 5%, about 10%, about 20% about 30%, about 50%, or about 90% lower than the lactate production of cells maintained in a culture medium that is substantially free from dextran sulfate or ferric citrate. In one embodiment, a cell culture described herein comprises between about 0.1 g/L and about 6 g/L, between about 0.1 g/L and about 5 g/L, between about 0.1 g/L and about 4 g/L, or between about 0.1 g/L and about 3 g/L of lactate. In another embodiment, a cell culture described herein comprises less than about 6 WI, about 5 g/L, about 4 g/L, about 3 g/L, about 2 g/L or about 1 g/L lactate.

The present invention also provides a method of decreasing ammonium production by a cell culture, comprising contacting the cell culture with a medium described herein. In one embodiment, the ammonium production of cells maintained in a culture medium described herein is between about 5% and about 90%, between about 5%, and about 80%, between about 5%, and about 70%, between about 5%, and about 50%, between about 5%, and about 40%, between about 5%, and about 30%, between about 5%, and about 20%, between about 10%, and about 90%, between about 20%, and about 90%, between about 30%, and about 90%, or between about 50%, and about 90%, or at least about 5%, at least about 10%, at least about 20%, at least about 30%, at least about 50%, or at least about 90%, or about 5%, about 10%, about 20%, about 30%, about 50%, or about 90% lower than the ammonium production of cells maintained in a culture medium that is substantially free from dextran sulfate or ferric citrate. In one embodiment, a cell culture described herein comprises between about 0.1 mM and about 20 mM, about 0.1 mM and about 15 mM, about 0.1 mM and about 14 mM, about 0.1 mM and about 13 mM, about 0.1 mM and about 12 mM, about 0.1 mM and about 11 mM, about 0.1 mM and about 10 mM, about 0.1 mM and about 9 mM, about 0.1 mM and about 8 mM, about 0.1 mM and about 7 mM, about 0.1 mM and about 6 mM, about 0.1 mM and about 5 mM, about 0.1 mM and about 4 mM, about 0.1 mM and about 3 mM, about 0.1 mM and about 2 mM, about 0.1 mM and about 1 mM, about 0.5 mM and about 20 mM, about 0.5 mM and about 15 mM, about 0.5 mM and about 14 mM, about 0.5 mM and about 13 mM, about 0.5 mM and about 12 mM, about 0.5 mM and about 11 mM, about 0.5 mM and about 10 mM, about 0.5 mM and about 9 mM, about 0.5 mM and about 8 mM, about 0.5 mM and about 7 mM, about 0.5 mM and about 6 mM, about 0.5 mM and about 5 mM, about 0.5 mM and about 4 mM, about 0.5 mM and about 3 mM, about 0.5 mM and about 2 mM, about 0.5 mM and about 1 mM, about 1 mM and about 20 mM, about 1 mM and about 15 mM, about 1 mM and about 14 mM, about 1 mM and about 13 mM, about 1 mM and about 12 mM, about 1 mM and about 11 mM, about 1 mM and about 10 mM, about 1 mM and about 9 mM, about 1 mM and about 8 mM, about 1 mM and about 7 mM about 1 mM and about 6 mM, about 1 mM and about 5 mM, about 1 mM and about 4 mM, about 1 mM and about 3 mM, or about 1 mM and about 2 mM ammonium. In another embodiment, a cell culture described herein comprises less than about 20 mM, about 19 mM, about 18 mM, about 17 mM, about 16 mM, about 15 mM, about 14 mM; about 13 mM, about 12 mM, about 11 mM, about 10 mM, about 9 mM, about 8 mM, about 7 mM, about 6 mM, about 5 mM, about 4 mM, about 3 mM, about 2 mM, about 1 mM, or about 0.5 mM ammonium.

The present invention further provides a method of producing a protein or polypeptide of interest, comprising culturing cells capable of producing the protein or polypeptide of interest in a culture comprising a medium described herein; and isolating the protein or polypeptide from the culture. In one embodiment, the protein or polypeptide of interest is a recombinant protein or polypeptide. In one embodiment, the protein or polypeptide of interest is an enzyme, receptor, antibody, hormone, regulatory factor, antigen, or binding agent. In a specific embodiment, the protein is an antibody, which can be, but is not limited to, a neublastin antibody, such as a monoclonal antibody.

In one embodiment of the present invention, a cell culture comprising a medium described herein can be maintained in production phase longer than a cell culture that does not comprise exogenous dextran sulfate. A skilled artisan readily understands that an extended production phase can lead to an increase in the total amount of polypeptide produce by the cell culture. In one embodiment, a method of producing a polypeptide of interest according to the present invention produces more polypeptide than the amount produced by a method that does not comprise maintaining cells capable of producing the polypeptide in a culture comprising exogenous dextran sulfate. In one embodiment, a method according to the present invention produces between about 5% and about 500%, about 5% and about 250%, about 5% and about 100%, about 5% and about 80%, about 5% and about 50%, about 5% and about 30%, about 10% and about 500%, about 20% and about 500%, about 30% and about 500%, about 50% and about 500%, or about 100% and about 500% more protein or polypeptide. In another embodiment, a method according to the present invention produces at least about 5%, at least about 10%, at least about 15%, at least about 20%, at least about 25%, at least about 30%, at least about 40%, at least about 50%, at least about 70%, at least about 90%, or at least about 100% more protein or polypeptide. In another embodiment, a method according to the present invention produces at least about 2 times, three times, four times, five times or ten times more protein or polypeptide. In a specific embodiment, the protein or polypeptide is an antibody.

In one embodiment, a method of producing a polypeptide of interest according to the present invention produces a higher titer of the polypeptide in the cell culture than the titer produced by a method that does not comprise maintaining the cells in a culture comprising dextran sulfate. In one embodiment, a method according to the present invention produces between about 5% and about 500%, about 5% and about 250%, about 5% and about 100%, about 5% and about 80%, about 5% and about 50%, about 5% and about 30%, about 10% and about 500%, about 20% and about 500%, about 30% and about 500%, about 50% and about 500%, or about 100% and about 500% higher titer. In another embodiment, a method according to the present invention produces at least about 5%, at least about 10%, at least about 15%, at least about 20%, at least about 25%, at least about 30%, at least about 40%, at least about 50%, at least about 70%, at least about 90%, or at least about 100% higher titer. In another embodiment, a method according to the present invention produces at least about 2 times, three times, four times, five times or ten times higher titer.

In a specific embodiment, the protein or polypeptide, is an antibody.

In a specific embodiment, a method of producing a polypeptide of interest according to the present invention produces a maximum protein or polypeptide titer of at least about 2 g/liter, at least about 2.5 g/liter, at least about 3 g/liter, at least about 3.5 g/liter, at least about 4 g/liter, at least about 4.5 g/liter, at least about 5 g/liter, at least about 6 g/liter, at least about 7 g/liter, at least about 3 g/liter, at least about 9 g/liter, or at least about 10 g/liter. In another embodiment, the method according to the present invention produces a maximum protein or polypeptide titer of between about 1 g/liter and about 10 g/liter, about 1.5 g/liter and about 10 g/liter, about 2 g/liter and about 10 g/liter, about 2.5 g/liter and about 10 g/liter, about 3 g/liter and about 10 g/liter, about 4 g/liter and about 10 g/liter, about 5 g/liter and about 10 g/liter, about 1 g/liter and about 5 g/liter, about 1 g/liter and about 4.5 g/liter, or about 1 g/liter and about 4 g/liter. In a specific embodiment, the protein or polypeptide is an antibody. In another embodiment, the protein or polypeptide is a blood clotting factor.

The invention further provides a conditioned cell culture medium produced by a method described herein.

In one embodiment, a conditioned cell culture medium according to the invention comprises a recombinant protein or polypeptide. In a specific embodiment, a conditioned cell culture medium according to the invention comprises a recombinant protein or polypeptide, at a titer of at least about 2 g/liter, at least about 2.5 g/liter, at least about 3 g/liter, at least about 3.5 g/liter, at least about 4 g/liter, at least about 4.5 g/liter at least about 5 g/liter, at least about 6 g/liter, at least about 7 g/liter, at least about 8 g/liter, at least about 9 g/liter, or at least about 10 g/liter, or a liter of between about 1 g/liter and about 10 g/liter, about 1.5 g/liter and about 10 g/liter, about 2 g/liter and about 10 g/liter, about 2.5 g/liter and about 10 g/liter, about 3 g/liter and about 10 g/liter, about 4 g/liter and about 10 g/liter, about 5 g/liter and about 10 g/liter, about 1 g/liter and about 5 g/liter, about 1 g/liter and about 4.5 g/liter, or about 1 g/liter and about 4 g/liter. In another embodiment, a conditioned cell culture medium according to the invention comprises recombinant protein or polypeptide at a higher titer than the titer obtained without the use of a medium described herein. In a specific embodiment, the protein or polypeptide is an antibody.

Polypeptides

Any polypeptide that is expressible in a host cell can be produced in accordance with the present invention. The polypeptide can be expressed from a gene that is endogenous to the host cell, or from a gene that is introduced into the host cell through genetic engineering. The polypeptide can be one that occurs in nature, or can alternatively have a sequence that was engineered or selected by the hand of man. An engineered polypeptide can be assembled from other polypeptide segments that individually occur in nature, or can include one or more segments that are not naturally occurring.

Polypeptides that can desirably be expressed in accordance with the present invention will often be selected on the basis of an interesting biological or chemical activity, for example, the present invention can be employed to express any pharmaceutically or commercially relevant enzyme, receptor, antibody, hormone, regulatory factor, antigen, binding agent, etc.

Particularly useful polypeptides are those that are highly negatively charged. Examples of highly negatively charged polypeptides include, but are not limited to, neublastin and Factor VIII.

Antibodies

Given the large number of antibodies currently in use or under investigation as pharmaceutical or other commercial agents, production of antibodies is of particular interest in accordance with the present invention. Antibodies are proteins that have the ability to specifically bind a particular antigen. Any antibody that can be expressed in a host cell can be used in accordance with the present invention. In one embodiment, the antibody to be expressed is a monoclonal antibody.

Particular antibodies can be made, for example, by preparing and expressing synthetic genes that encode the recited amino acid sequences or by mutating human germline genes to provide a gene that encodes the recited amino acid sequences. Moreover, these antibodies can he produced, e.g., using one or more of the following methods.

Numerous methods are available for obtaining antibodies, particularly human antibodies. One exemplary method includes screening protein expression libraries, e.g. phage or ribosome display libraries. Phage display is described, for example, U.S. Pat. No. 5,223,409; Smith (1985) Science 228:1315-1317; WO 92/18619; WO 91/17271; WO 92/20791; and WO 90/02809. The display of Fab's on phage is described, e.g., in U.S. Pat. Nos. 5,658,727; 5,667,988; and 5,885,793.

In addition to the use of display libraries, other methods can be used to obtain an antibody. For example, a protein or a peptide thereof can be used as an antigen in a non-human animal, e.g., a rodent, e.g., a mouse, hamster, or rat.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity can be produced and selected. See, e.g., XENOMOUSE™, Green et al. (1994) *Nature Genetics* 7:13-21, U.S. 2003-0070185, WO 96/34096, and WO 96/33735.

In another embodiment, a monoclonal antibody is obtained from the non-human animal, and then modified, e.g., humanized or deimmunized. Winter describes an exemplary CDR grafting method that can be used to prepare humanized antibodies described herein (U.S. Pat. No. 5,225,539). All or some of the CDRs of a particular human antibody can be replaced with at least a portion of a non-human antibody. In one embodiment, it is only necessary to replace the CDRs required for binding or binding determinants of such CDRs to arrive at a useful humanized antibody that binds to an antigen.

Humanized antibodies can be generated by replacing sequences of the Fv variable region that are not directly involved in antigen binding with equivalent sequences from human Fv variable regions, General methods for generating humanized antibodies are provided by Morrison, S. L. (1985) *Science* 229:1202-1207, by Oi et al. (1986) *BioTechniques* 4:214, and by U.S. Pat. Nos. 5,585,089; 5,693,761; 5,693,762; 5,859,205; and 6,407,213. Those methods include isolating, manipulating, and expressing the nucleic-acid sequences that encode all or part of immunoglobulin Fv variable regions from at least one of a heavy or light chain. Sources of such nucleic acid are well known to those skilled in the art and, for example, can be obtained from a hybridoma producing an antibody against a predetermined target, as described above, from germline immunoglobulin genes, or from synthetic constructs. The recombinant DNA encoding the humanized antibody can then be cloned into an appropriate expression vector. In one embodiment, the expression vector comprises a polynucleotide encoding a glutamine synthetase polypeptide. (See, e.g., Porter et al., *Biotechnol Prog* 26(5):1446-54 (2010).

The antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG constant region can be mutated at one or more residues, e.g., one or more of residues 234 and 237. Antibodies can have mutations in the CH2 region of the heavy chain that reduce or alter effector function, e.g., Fc receptor binding and complement activation. For example, antibodies can have mutations such as those described in U.S. Pat. Nos. 5,624,821 and 5,648,260. Antibodies can also have mutations that stabilize the disulfide bond between the two heavy chains of an immunoglobulin, such as mutations in the hinge region of IgG14, as disclosed in the art (e.g., Angal et. al, (1993) *Mol. Immunol.* 30:105-08). See also, e.g., U.S. 2005-0037000.

In other embodiments, the antibody can be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies can be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) *CRC Crit, Rev. Biochem.* 22:259-306. Removal of any carbohydrate moieties present on the antibodies can be accomplished chemically or enzymatically as described in the art (Hakimuddin et al, (1987) *Arch. Biochem. Biophys.* 259:52; Edge et al. (1981) *Anal. Biochem.* 118:131; and Thotakura et al. (1987) *Meth. Enzymol,* 138:350), See, e.g., U.S. Pat. No. 5,869,046 for a modification that increases in vivo half-life by providing a salvage receptor binding epitope.

The antibodies can be in the form of full length antibodies, or in the form of fragments of antibodies, e.g., Fab, F(ab')2, Fd, dAb, and scFv fragments. Additional forms include a protein that includes a single variable domain, e.g., a camelid or camelized domain. See, e.g., U.S. 2005-0079574 and Davies et al, (1996) *Protein Eng.* 9(6):531-7.

In one embodiment, the antibody is an antigen-binding fragment of a full length antibody, e.g., a Fab, F(ab')2, Fv, or a single chain Fv fragment. Typically, the antibody is a full length antibody. The antibody can be a monoclonal antibody or a mono specific antibody.

In another embodiment, the antibody can be a human, humanized, CDR-grafted, chimeric, mutated, affinity matured, deimmunized, synthetic or otherwise in vitro-generated antibody, and combinations thereof.

The heavy and light chains of the antibody can be substantially full-length. The protein can include at least one, and preferably two, complete heavy chains, and at least one, and preferably two, complete light chains) or can include an antigen-binding fragment (e.g., a Fab, F(ab')2, Fv or a single chain Fv fragment). In yet other embodiments, the antibody has a heavy chain constant region chosen from, e.g., IgG1, IgG2, IgG13, IgG4, IgM, IgGA1, IgA2, IgD, and IgE; particularly, chosen from, e.g., IgG1, IgG2, IgG3, and IgG4, more particularly, IgG1 (e.g., IgG1). Typically, the heavy chain constant region is human or a modified form of a human constant region. In another embodiment, the antibody has a light chain constant region chosen from, e.g., kappa or lambda, particularly, kappa (e.g., human kappa).

Receptors

Another class of polypeptides that have been shown to be effective as pharmaceutical and/or commercial agents includes receptors. Receptors are typically trans-membrane glycoproteins that function by recognizing an extra-cellular signaling ligand. Receptors typically have a protein kinase domain in addition to the ligand recognizing domain, which initiates a signaling pathway by phosphorylating target intracellular molecules upon binding the ligand, leading to developmental or metabolic changes within the cell. In one embodiment, the receptors of interest are modified so as to remove the transmembrane and/or intracellular domain(s), in place of which there can optionally be attached an Ig-domain. In one embodiment, receptors to be produced in accordance with the present invention are receptor tyrosine kinases (RTKs). The RTK family includes receptors that are crucial for a variety of functions numerous cell types (see, e.g., Yarden and Ullrich, *Ann. Rev. Biochem.* 57:433-478, 1988; Ullrich and Schlessinger (1990) *Cell* 61:243,254). Non-limiting examples of RTKs include members of the fibroblast growth factor (FGF) receptor family, members of the epidermal growth factor receptor (EGF) family, platelet derived growth factor (PDGF) receptor, tyrosine kinase with immunoglobulin and EGF homology domains-1 (TIE-1) and TIE-2 receptors (Sato et al., *Nature* 376(6535):70-74 (1995), incorporated herein by reference) and c-Met receptor, some of which have been suggested to promote angiogenesis, directly or indirectly (Mustonen and Alitalo, *J. Cell Biol.* 129:895-898, 1995). Other non-limiting examples of RTK's include fetal liver kinase 1 (FLK-1) (sometimes referred to as kinase insert domain-containing receptor (KDR) (Terman et al., *Oncogene* 6:1677-83, 1991) or vascular endothelial cell growth factor receptor 2 (VEGFR-2)), fins-like tyrosine kinase-1 (Flt-1) (DeVries et al, *Science* 255:989-991, 1992; Shibuya et al., *Oncogene* 5:519-524, 1990), sometimes referred to as vascular endothelial cell growth factor receptor 1 (VEGFR-1), neuropilin-1, endoglin, endosialin, and Axl. Those of ordinary skill in the art will be aware of other receptors that can be expressed in accordance with the present invention.

Growth Factors and Other Signaling Molecules

Another class of polypeptides that have been shown to be effective as pharmaceutical and/or commercial agents includes growth factors and other signaling molecules. Growth factors are typically glycoproteins that are secreted by cells and bind to and activate receptors on other cells, initiating a metabolic or developmental change in the receptor cell.

Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I, and -II (IGF-I and IGF-II); des(1-3)-IGF-I (brain IGF-I), insulin-like growth factor binding proteins; CD proteins such as CD-3., CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (TLs), e.g., IL-1 to IL-10; tumor necrosis factor (TNF) alpha and beta; insulin A-chain; insulin B-chain; proinsulin; follicle stimulating hormone; calcitonin; luteinizing hormone; glucagon; anti-clotting factors such as Protein C; atrial natriuretic factor; lung surfactant; a plasminogen activator, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; prorelaxin; mouse gonadotropin-associated peptide; neurotrophic factors such as bone-derived neurotrophic factor (BDNF), neurotrophin-3, -4, -5, or -6 (NT-3, NT-4, NT-5, or NT-6), or a nerve growth factor such as NGF-beta, One of ordinary skill in the art will be aware of other growth factors or signaling molecules that can be expressed in accordance with the present invention.

Clotting Factors

In some embodiments, the protein of interest comprises a clotting factor. "Clotting factor", as used herein, means any molecule, or analog thereof, which prevents or decreases the duration of a bleeding episode in a subject with a hemostatic disorder. For example, a clotting factor for the invention can be a full-length clotting factor, a mature clotting factor, or a chimeric clotting factor. In other words, it means any molecule having clotting activity. Clotting activity, as used herein, means the ability to participate in a cascade of biochemical reactions that culminates in the formation of a fibrin clot and/or reduces the severity, duration or frequency of hemorrhage or bleeding episode. Examples of clotting factors can be found in U.S. Pat. No. 7,404,956.

In one embodiment, the clotting factor is Factor VIII, Factor IX, Factor XI, Factor XII, fibrinogen, prothrombin, Factor V, Factor VII, Factor X, Factor XIII or von Willebrand Factor. The clotting factor can be a factor that participates in the extrinsic pathway. The clotting factor can be a factor that participates in the intrinsic pathway. Alternatively, the clotting factor can be a factor that participates in both the extrinsic and intrinsic pathway.

In one embodiment, the clotting factor can be a non-human clotting factor or a non-human clotting factor, e.g., derived from a non-human primate, a pig or any mammal. The clotting factor can be chimeric clotting factor, e.g., the clotting factor can comprise a portion of a human clotting factor and a portion of a porcine clotting factor or a portion of a first non-human clotting factor and a portion of a second non-human clotting factor.

In another embodiment, the clotting factor can be an activated clotting factor. Alternatively, the clotting factor can be an inactive form of a clotting factor, e.g., a zymogen. The inactive clotting factor can undergo activation subsequent to being linked to at least a portion of an immunoglobulin constant region. The inactive clotting factor can be activated subsequent to administration to a subject. Alternatively, the inactive clotting factor can be activated prior to administration.

In certain embodiments, the clotting factor is a Factor VIII protein. "Factor VIII protein" or "FVIII protein" as used herein, means functional Factor VIII protein in its normal role in coagulation, unless otherwise specified. Thus, the term FVIII includes variant proteins that are functional. In one embodiment, the FVIII protein is the human, porcine, canine, rat, or marine FVIII protein. A functional FVIII protein can be a fusion protein, such as, but not limited to, a fusion protein comprising a fully or partially B-domain deleted FVIII, at least a portion of an immunoglobulin constant region, e.g., an Fc domain, or both. Myriad functional FVIII variants have been constructed and can be used as recombinant FVIII proteins as described herein, See PCT Publication Nos. WO 2011/069164 A2, WO 2012/006623 A2, WO 2012/006635 A2, or WO 2012/006633 A2, all of which are incorporated herein by reference in their entireties.

A great many functional FVIII variants are known. In addition, hundreds of nonfunctional mutations in FVIII have been identified in hemophilia patients. See, e.g., Cutler et al., Hum. Mutat. 19:274-8 (2002), incorporated herein by reference in its entirety. In addition, comparisons between FVIII from humans and other species have identified conserved residues that are likely to be required for function. See, e.g., Cameron et al., Thromb. Haemost. 79:317-22 (1998) and U.S. Pat. No. 6,251,632, incorporated herein by reference in their entireties.

In certain aspects, a recombinant FVIII protein of the invention is chimeric. A "chimeric protein," or "chimeric polypeptide" as used herein, means a protein or polypeptide that includes within it at least two stretches of amino acids from different sources, e.g., a FVIII protein comprising a heterologous moiety. In one embodiment, the heterologous moiety can be a half-life extending moiety. Examples of the heterologous moieties include, but are not limited to, an immunoglobulin constant region or a fragment thereof, e.g., an Fc region or an FeRn binding partner, a VWF molecule, or a fragment thereof, albumin, albumin binding polypeptide, Fc, PHS, the β subunit of the C-terminal peptide (CTP) of human chorionic gonadotropin, polyethylene glycol (PEG), hydroxyethyl starch (HES), albumin-binding small molecules, or combinations thereof. In some embodiments, the chimeric protein is a FVIII monomer dimer hybrid.

A long-acting or long-lasting FIX polypeptide useful for the invention is a chimeric polypeptide comprising a FIX polypeptide and an FcRn binding partner. The FIX polypeptide of the invention comprises a functional Factor IX polypeptide in its normal role in coagulation, unless otherwise specified. Thus, the FIX polypeptide includes variant polypeptides that are functional and the polynucleotides that encode such functional variant polypeptides. In one embodiment, the FIX polypeptides are the human, bovine, porcine, canine, feline, and murine FIX polypeptides. The full length polypeptide and polynucleotide sequences of FIX are known, as are many functional variants, e.g., fragments, mutants and modified versions. FIX polypeptides include full-length FIX, full-length FIX minus Met at the N-terminus, full-length FIX minus the signal sequence, mature, FIX (minus the signal sequence and propeptide), and mature FIX with an additional Met at the N-terminus. FIX can be made by recombinant means ("recombinant Factor IX" or "rFIX"), i.e., it is not naturally occurring or derived from plasma.

The clotting factor can also include a FIX protein or any variant, analog, or functional fragments thereof. A great many functional FIX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses FIX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant FIX molecules that exhibit increased protein stability, increased in vivo and in vitro half-life, and increased resistance to proteases at page 4, line 1 to page 19, line 11. WO 2007/149406 A2 also discloses chimeric and other variant FIX molecules at page 19, line 12 to page 20, line 9. International Pub. no WO 08/118507 A2, which is herein incorporated by reference in its entirety, discloses FIX mutants that exhibit increased clotting activity at page 5, line 14 to page 6, line 5. International Pub. no WO 09/051717 A2, discloses FIX mutants having an increased number of N.-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International Pub. no WO 09/130198 A2, which is herein incorporated by reference in its entirety, discloses functional mutant FIX molecules that have an increased number of glycosylation sites, which result in an increased half-life, at page 4, line 26 to page 12, line 6. International Pub. no WO 09/140015 A2, which is herein incorporated by reference in its entirety, discloses functional FIX mutants that an increased number of Cys residues, which may be used for polymer (e.g., PEG) conjugation, at page 11, paragraph [0043] to page 13, paragraph [0053]. The FIX polypeptides described in International Application No. PCT/US2011/043569 filed Jul. 11, 2011 and published as WO 2012/006624 on Jan. 12, 2012 are also incorporated herein by reference in its entirety.

In addition, hundreds of non-functional mutations in FIX have been identified in hemophilia patients, many of which are disclosed in Table 1, at pages 11-14 of International Pub. no WO 09/137254 A2, which is herein incorporated by reference in its entirety. Such non-functional mutations are not included in the invention, but provide additional guidance for which mutations are more or less likely to result in a functional FIX polypeptide.

In some embodiments, the chimeric protein of the invention is a FIX monomerdimer hybrid. Monomer-dimer hybrid can comprise two polypeptide chains, one chain comprising a FIX polypeptide and a first Fc region, and another chain comprising, consisting essentially of, or consisting of a second Fc region. In certain aspects, a FIX monomer dimer hybrid consists essentially of or consists of two polypeptide chains, a first chain consisting essentially of or consisting of a FIX polypeptide and a second chain consisting essentially of or consisting of a second Fc region.

In some embodiments, a clotting factor is a mature form of Factor VII or a variant thereof. Factor VII (F-VII, F7; also referred to as Factor 7, coagulation factor VII, serum factor VII, serum prothrombin conversion accelerator, SPCA, proconvertin and eptacog alpha) is a serine protease that is part of the coagulation cascade. FVII includes a Gla domain, two EGF domains (EGF-1 and EGF-2), and a serine protease domain (or peptidase S1 domain) that is highly conserved among all members of the peptidase S1 family of serine proteases, such as for example with chymotrypsin. FVII occurs as a single chain zymogen, an activated zymogen-like two-chain polypeptide and a fully activated two-chain form.

Exemplary FVII variants include those with increased specific activity, e.g., mutations that increase the activity of FVII by increasing its enzymatic activity (Kcat or Km). Such variants have been described in the art and include, e.g., mutant forms of the molecule as described for example in Persson et al., 2001, *PNAS* 98:13583; Petrovan and Ruf, 2001. *J. Biol, Chem.* 276:6616; Persson et al., 2001 *J. Biol. Chem.* 276:29195; Soejima et al., 2001, *J. Biol. Chem.* 276:17229; Soejima et al., 2002, *J. Biol. Chem.* 247:49027.

In one embodiment, a variant form of FV1I includes the mutations. Exemplary mutations include V158D-E296V-M298Q. In another embodiment, a variant form of -FVII includes a replacement of amino acids 608-619 (LQQSRKVGDSPN, corresponding to the 170-loop) from the FVII mature sequence with amino acids EASYPGK from the 170-loop of trypsin, High specific activity variants of FIX are also known-in the art. For example, Simioni et al., 2009 N.E. *J. Med.* 361:1671) describe an R338L, mutation. Chang et al. (1988 *JBC* 273:12089) and Pierri et al., (20.09 *Human Gene Therapy* 20:479) describe an R338A mutation. Other mutations are known in the art and include those described, e.g., in Zogg and Brandstetter. 2009 *Structure* 17:1669; Sichler et al., 2003, *J. Biol. Chem.* 278:4121; and Sturzebecher et al., 1997, *FEBS Lett* 412:295. The contents of these references are incorporated herein by reference.

Full activation, which occurs upon conformational change from a zymogen-like form, occurs upon binding to is cofactor tissue factor. Also, mutations can be introduced that result in the conformation change in the absence of tissue factor. Hence, reference to FVIIa includes both two-chain forms thereof: the zymogen-like form (e.g., activatable FVII), and the fully activated two-chain form.

Various patents or applications disclosing examples of the clotting factors useful for the invention are incorporated herein by reference. For example, various monomer dimer hybrid constructs comprising clotting factors (FVII, FIX, and FVIII) are disclosed in U.S. Pat. Nos. 7,404,945, 7,348,004, 7,862,820, 8,329,182, and 7,820,162, incorporated herein by reference in their entireties, Examples of FVIII chimeric protein are additionally disclosed in US Appl. Nos. 61/734,954 or 61/670,553, incorporated by reference in its entirety. Examples of FVII chimeric protein are disclosed in U.S. Appln. No. 61/657,688.

G-Protein Coupled Receptors

Another class of polypeptides that have been shown to be effective as pharmaceutical and/or commercial agents includes growth factors and other signaling molecules. G-protein coupled receptors (GPCRs) are proteins that have seven transmembrane domains. Upon binding of a ligand to a GPCR, a signal is transduced within the cell which results in a change in a biological or physiological property of the cell.

GPCRs, along with G.-proteins and effectors (intracellular enzymes and channels which are modulated by G-proteins), are the components of a modular signaling system that connects the state of intracellular second messengers to extracellular inputs. These genes and gene-products are potential causative agents of disease.

The GPCR protein superfamily now contains over 250 types of paralogues, receptors that represent variants generated by gene duplications (or other processes), as opposed to orthologues, the same receptor from different species, The superfamily can be broken down into five families; Family I, receptors typified by rhodopsin and the beta2-adrenergic receptor and currently represented by over 200 unique members; Family II, the recently characterized parathyroid hormone/calcitonin/secretin receptor family; Family III, the metabotropic glutamate receptor family in mammals; Family IV, the cANIP receptor family, important in the chemotaxis and development of *D. discoideum*; and Family V, the fungal mating pheromone receptors such as STE2.

Viruses

Additionally, the present invention also provides methods for the production of viruses using a cell culture according to methods known to those of skill in the field of virology. The viruses to be produced in accordance with the present invention can be chosen from the range of viruses known to infect the cultured, cell type. For instance, when utilizing a mammalian cell culture, viruses can be chosen from the genera of orthomyxoviruses, paramyxoviruses, reoviruses, picornaviruses, flaviviruses, arenaviruses, herpesviruses, poxviruses, coronaviruses and adenoviruses. The virus used can be a wild-type virus, an attenuated virus, a reassortant virus, or a recombinant virus. In addition, instead of actual virions being used to infect the cells with a virus, an infectious nucleic acid clone can be utilized according to infectious clone transfection methods known to those of skill in the field of virology. In one embodiment, the virus produced is an influenza virus.

Cells

Any eukaryotic cell or cell type susceptible to cell culture can be utilized in accordance with the present invention. For example, plant cells, yeast cells, animal cells, insect cells, avian cells or mammalian cells can be utilized in accordance with the present invention. In one embodiment, the eukaryotic cells are capable of expressing a recombinant protein or are capable of producing a recombinant or reassortant virus.

Non-limiting examples of mammalian cells that can be used in accordance with the present invention include BALB/c mouse myeloma line (NSO/1, ECACC No: 85110503); human retinoblasts (PER,C6 (CruCell, Leiden, The Netherlands)); monkey kidney CVI line transformed by SV40 (COS-7, ATCC CRL 1651); human embryonic kidney line (293 or 293 cells subcloned for growth in suspension culture, Graham et al., *J. Gen. Virol.,* 36:59 (1977)); baby hamster kidney cells (BHK, ATCC CCL 10); Chinese hamster ovary cells ±DHFR (CHO, Urlaub and Chasin, *Proc., Natl. Acad. Sci. USA,* 77:4216 (1980)); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL5 1); TRI cells (Mather et al., *Annals N.Y. Acad. Sci.* 383:44-68 (1982)); MRC 5 cells; FS4 cells; and a human hepatoma line (Hep G2). In one embodiment, the present invention is used in the culturing of and expression of polypeptides from CHO cell lines. In a specific embodiment, the CHO cell line is the DG44 CHO cell line. In a specific embodiment, the CHO cell line comprises a vector comprising a polynucleotide encoding a glutamine synthetase polypeptide. In a further specific embodiment, the CHO cell line expresses an exogenous glutamine synthetase gene. (See, e.g., Porter et al., *Biotechnol. Prog.* 26(5):1446-54 (2010)). In yet other embodiments, the CHO cell line comprises a vector comprising a polynucleotide encoding a neublastin antibody or fragment thereof.

Additionally, any number of commercially and non-commercially available hybridoma cell lines that express polypeptides or proteins can be utilized in accordance with the present invention. One skilled in the art will appreciate that hybridoma cell lines might have different nutrition requirements and/or might require different culture conditions for optimal growth and polypeptide or protein expression, and will be able to modify conditions as needed, The eukaryotic cells according to the present invention can be selected or engineered to produce high levels of protein or polypeptide, or to produce large quantities of virus. Often, cells are genetically engineered to produce high levels of protein, for example by introduction of a gene encoding the protein or polypeptide of interest and/or by introduction of control elements that regulate expression of the gene (whether endogenous or introduced) encoding the polypeptide of interest.

The eukaryotic cells eau also be selected or engineered to survive in culture for extended periods of time. For example, the cells can be genetically engineered to express a polypeptide or polypeptides that confer extended survival on the cells. In one embodiment, the eukaryotic cells comprise a transgene encoding the Bcl-2 polypeptide or a variant thereof. See, e.g., U.S. Pat. No. 7,785,880. In a specific embodiment, the cells comprise a polynucleotide encoding the bol-xL polypeptide. See, e.g., Chiang G G, Sisk W P. 2005. *Biotechnol. Bioeng.* 91(7):779-792.

The eukaryotic cells can also be selected or engineered to modify its posttranslational modification pathways. In one embodiment, the cells are selected or engineered to modify a protein glycosylation pathway. In a specific embodiment, the cells are selected or engineered to express an aglycosylated protein, e.g., an aglycosylated recombinant antibody. In another specific embodiment, the cells are selected or engineered to express an afucosylated protein, e.g., an afucosylated recombinant antibody.

The eukaryotic cells can also be selected or engineered to allow culturing in serum free medium.

Media

The cell culture of the present invention is prepared in any medium suitable for the particular cell being cultured. In some embodiments, the medium contains e.g., inorganic salts, carbohydrates (e.g., sugars such as glucose, galactose, maltose or fructose), amino acids, vitamins (e.g., B group vitamins (e.g., B12), vitamin A vitamin E, riboflavin, thiamine and biotin); fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, copper, selenium and tricarboxylic acid intermediates), hydrolysates (hydrolyzed proteins derived from plant or animal sources), and combinations thereof. Commercially available media such as Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions. In addition, any of the media described in Ham and Wallace, (1979)*Meth. Enzymol.* 58:44; Barnes and Sato, (1980) *Anal. Biochem.* 102:255; U.S. Pat. Nos. 4,767,704; 4,657,866; 4,927,762; 5,122,469 or 4,560,655; International Publication Nos. WO 90/03430; and WO 87/00195; the disclosures of all of which are incorporated herein by reference, can be used as culture media. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and their suitable carriers, and glucose or an equivalent energy source. In some embodiments the nutrient media is serum-free media, a protein-free media, or a chemically defined media. Any other necessary supplements can also be included at appropriate concentrations that would be known to those skilled in the art.

In one embodiment, the mammalian host cell is a CHO cell and a suitable medium contains a basal medium component such as a DMEM/HAM F-12 based formulation (for composition of DMEM and HAM F12 media, see culture media formulations in *American Type Culture Collection Catalogue of Cell Lines and Hybridomas*, Sixth Edition, 1988, pages 346-349) with modified concentrations of some components such as amino acids, salts, sugar, and vitamins, and optionally containing glycine, hypoxanthine, and thymidine; recombinant human insulin, hydrolyzed peptone, such as Primatone HS or Primatone RL (Sheffield, England), or the equivalent; a cell protective agent, such as Pluronic F68 or the equivalent pluronic polyol; gentamycin; and trace elements.

The present invention provides a variety of media formulations that, when used in accordance with other culturing steps described herein, minimize, prevent or reverse metabolic imbalances in the culture that would lead to increased lactate and ammonium production.

A media formulation of the present invention that have been shown to have beneficial effects on metabolic balance, cell growth and/or viability or on expression of polypeptide or protein comprise dextran sulfate. One of ordinary skill in the art will understand that the media formulations of the present invention encompass both defined and non-defined media.

Cell Culture Processes

Various methods of preparing mammalian cells for -production of proteins or polypeptides by batch and fed-batch culture are well known in the art. A nucleic acid sufficient to achieve expression (typically a vector containing the gene encoding the polypeptide or protein of interest and any operably linked genetic control elements) can be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include but are not limited to immunohistochemistry, immunoprecipitation, flow cytometry, immunofluorescence microscopy, SDS-PAGE, Western blots, enzyme-linked immunosorbent assay (ELISA), high performance liquid chromatography (HPLC) techniques, biological-activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

Once a cell that expresses the polypeptide or protein of interest has been identified, the cell is propagated in culture by any of the variety of methods well-known to one of ordinary skill in the art. The cell expressing the polypeptide of interest is typically propagated by growing it at a temperature and in a medium, that is conducive to the survival, growth and viability of the cell. The initial culture volume can be of any size, but is often smaller than the culture volume of the production bioreactor used in the final production of the polypeptide or protein of interest, and frequently cells are passaged several times in bioreactors of increasing volume prior to seeding the production bioreactor. The cell culture can be agitated or shaken to increase oxygenation of the medium and dispersion of nutrients to the cells. Alternatively, or additionally, special sparging devices that are well known in the art can be used to increase and control oxygenation of the culture. In accordance with the present invention, one of ordinary skill in the art will understand that it can be beneficial to control or regulate certain internal conditions of the bioreactor, including but not limited to pH, temperature, oxygenation, etc.

The cell density useful in the methods of the present invention can be chosen by one of ordinary skill in the art. In accordance with the present invention, the cell density can be as low as a single cell per culture volume. In some embodiments of the present invention, starting cell densities can range from about $2\times10^2$ viable cells per mL to about $2\times10^3$, $2\times10^4$, $2\times10^5$, $2\times10^6$, $5\times10^6$ or $10\times10^6$ viable cells per mL and higher.

In accordance with the present invention, a-cell culture size can be any volume that is appropriate for production of polypeptides. In one embodiment, the volume of the cell culture is at least 500 liters. In other embodiments, the volume or the production cell culture is 10, 50, 100, 250, 1000, 2000, 2500, 5000, 8000, 10,000, 12,000 liters or more, or any volume in between. For example, a cell culture will be 10 to 5,000 liters, 10 to 10,000 liters, 10 to 15,000 liters, 50 to 5,000 liters, 50 to 10,000 liters, or 50 to 15,000 liters, 100 to 5,000 liters, 100 to 10,000 liters, 100 to 15,000 liters, 500 to 5,000 liters, 500 to 10,000 liters, 500 to 15,000 liters, 1,000 to 5,000 liters, 1,000 to 10,000 liters, or 1,000 to 15,000 liters. Alternatively, a cell culture will be between about 500 liters and about 30,000 liters, about 500 liters and about 20,000 liters, about 500 liters and about 10,000 liters, about 500 liters and about 5,000 liters, about 1,000 titers and about 30,000 liters, about 2,000 liters and about 30,000 liters, about 3,000 liters and about 30,000 liters, about 5,000 liters and about 30,000 liters, or about 10,000 liters and about 30,000 liters, or a cell culture will be at least about 500 liters, at least about 1,000 liters, at least about 2,000 liters, at least about 3,000 liters, at least about 5,000 liters, at least about 10,000 liters, at least about 15,000 liters, or at least about 20,000 liters.

One of ordinary skill in the art will be aware of and will be able to choose a suitable culture size for use in practicing the present invention. The production bioreactor for the culture can be constructed of any material that is conducive to cell growth and viability that does not interfere with expression or stability of the produced polypeptide or protein.

The temperature of the cell culture will be selected based primarily on the range of temperatures at which the cell culture remains viable. For example, during the initial growth phase, CHO cells grow well at 37° C. In general, most mammalian cells grow well within a range of about 25° C. to 42° C.

In one embodiment of the present invention, the temperature of the initial growth phase is maintained at a single, constant temperature. In another embodiment, the temperature of the initial growth phase is maintained within a range of temperatures. For example, the temperature can be steadily increased or decreased during the initial growth phase. Alternatively, the temperature can be increased or decreased by discrete amounts at various times during the initial, growth phase. One of ordinary skill in the art will be able to determine whether a single or multiple temperature should be used, and whether the temperature should be adjusted steadily or by discrete amounts.

The cells can be grown during the initial growth phase for a greater or lesser amount of time, depending on the needs of the practitioner and the requirement of the cells themselves. In one embodiment, the cells are grown for a period of time sufficient to achieve a viable cell density that is a given percentage of the maximal viable cell density that the cells would eventually reach if allowed to grow undisturbed. For example, the cells can be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In another embodiment the cells are allowed to grow for a defined period of time. For example, depending on the starting concentration of the cell culture, the temperature at which the cells are grown, and the intrinsic growth rate of the cells, the cells can be grown for 0, 1, 2, 3, 4, 5, 6, 7, 8, 9, 10, 11, 12, 13, 14, 15, 16, 17, 18, 19, 20 or more days. In some cases, the cells can be allowed to grow for a month or more. In one embodiment, the growth phase is between about 1 day and about 20 days, about 1 day and about 15 days, about 1 day and about 14 days, about 1 day and about 13 days, about 1 day and about 12 days, about 1 day and about 11 days, about 1 day and about 10 days, about 1 day and about 9 days, about 1 day and about 8 days, about 1 day and about 7 days, about 1 day and about 6 days, about 1 day and about 5 days, about 1 day and about 4 days, about 1 day and about 3 days, about 2 clays and about 15 days, about 3 days and about 15 days, about 4 days and about 15 days, about 5 days and about 15 days, about 6 days and about 15 days, about 7 days and about 15 days, about 8 days and about 15 days, about 9 days and about 15 days, about 10 days and about 15 days, about 2 days and about 20 days, about 3 days and about 20 days, about 4 days and about 20 days, about 5 days and about 20 days, about 6 days and about 20 days, about 7 days and about 20 days, about 8 days and about 20 days, about 9 days and about 20 days, about 10 days and about 20 days, or about 10 days and about 20 days. In another embodiment, the growth phase is at least about 1 day, at least about 2 days, at least about 3 days, at least about 4 days, at least about 5 days, at least about 6 days, at least about 7 days, at least about 8 days, at least about 9 clays, at least about 10 days, at least about 11 days, at least about 12 days, at least about 15 days, or at least about 20 days. In a further embodiment, the growth phase is about 1 day, about 2 days, about 3 days, about 4 days, about 5 days, about 6 days, about 7 days, about 8 days, about 9 days, about 10 days, about 11 days, about 12 days, about 15 days, or about 20 days.

The cells would be grown for 0 days in the production bioreactor if their growth in a seed bioreactor, at the initial growth phase temperature, was sufficient that the viable cell density in the production bioreactor at the time of its inoculation is already at the desired percentage of the maximal viable cell density. The practitioner of the present invention will be able to choose the duration of the initial growth phase depending on polypeptide or protein production requirements and the needs of the cells themselves.

The cell culture can be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

In one embodiment, at the end of the initial growth phase, at least one of the culture conditions is shifted so that a second set of culture conditions is applied. The shift in culture conditions can be accomplished by a change in the temperature, pH, osmolality or chemical inductant level of the cell culture. In one embodiment, the culture conditions are shifted by shifting the temperature of the culture.

When shifting the temperature of the culture, the temperature shift can be relatively gradual. For example, it can take several hours or days to complete the temperature change. Alternatively, the temperature shift can be relatively abrupt. For example, the temperature change can be complete in less than several hours. Given the appropriate production and control equipment, such as is standard in the commercial large-scale production of polypeptides or proteins, the temperature change can even be complete within less than an hour.

The temperature of the cell culture in the subsequent growth phase will be selected based primarily on the range of temperatures at which the cell culture remains viable and expresses recombinant polypeptides or proteins at commercially adequate levels. In general, most mammalian cells remain viable and express recombinant polypeptides or proteins at commercially adequate levels within a range of about 25° C. to 42° C. In one embodiment, mammalian cells remain viable and express recombinant polypeptides or proteins at commercially adequate levels within a range of about 25° C. to 35° C. Those of ordinary skill in the art will be able to select appropriate temperature or temperatures in which to grow cells, depending on the needs of the cells and the production requirements of the practitioner.

In accordance with the present invention, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture can be shifted by shifting one or more of a number of culture conditions including, but not limited to, temperature, pH, osmolality, and sodium butyrate levels. In one embodiment, the temperature of the culture is shifted. According to this embodiment, during the subsequent production phase, the culture is maintained at a temperature or temperature range that is lower than the temperature or temperature range of the initial growth phase. For example, during the subsequent production phase, CHO cells express recombinant polypeptides and proteins well within a range of 25° C. to 35° C.

In accordance with the present invention, the cells can be maintained in the subsequent production phase until a desired cell density or production titer is reached. In one embodiment, the cells are maintained in the subsequent production phase until the titer to the recombinant polypeptide or protein reaches a maximum. In other embodiments, the culture can be harvested prior to this point, depending on the production requirement of the practitioner or the needs of the cells themselves. For example, the cells can be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it is desirable to allow the viable cell density to reach a maximum, and then allow the viable cell density to decline to some level before harvesting the culture. In an extreme example, it can be desirable to allow the viable cell density to approach or reach zero before harvesting the culture.

In another embodiment of the present invention, the cells are allowed to grow for a defined period of time during the subsequent production phase. For example; depending on the concentration of the cell culture at the start of the subsequent growth phase, the temperature at which the cells are grown, and the intrinsic growth rate of the cells, the cells can be grown for 1, 2, 3, 4, 5, 6, 7, 8, 9, 10, 11, 12, 13, 14, 15, 16, 17, 18, 19, 20 or more days. In some cases, the cells can be allowed to grow for a month or more. The practitioner of the present invention will be able to choose the duration of the subsequent production phase depending on polypeptide or protein production requirements and the needs of the cells themselves.

In certain cases, it can be beneficial or necessary to supplement the cell culture during the growth and/or subsequent production phase with nutrients or other medium components that have been depleted or metabolized by the cells. For example, it might be advantageous to supplement the cell culture with nutrients or other medium components observed to have been depleted. Alternatively, or additionally, it can be beneficial or necessary to supplement the cell culture prior to the subsequent production phase. As non-limiting examples, it can be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

These supplementary components, including the amino acids, can all be added to the cell culture at one time, or they can be provided to the cell culture in a series of additions. In one embodiment of the present invention, the supplementary components are provided to the cell culture at multiple times in proportional amounts. In another embodiment, it can be desirable to provide only certain of the supplementary components initially, and provide the remaining components at a later time. In yet another embodiment of the present invention, the cell culture is fed continually with these supplementary components.

In accordance with the present invention, the total volume added to the cell culture should optimally be kept to a minimal amount. For example, the total volume of the medium or solution containing the supplementary components added to the cell culture can be 1, 2, 3, 4, 5, 6, 7, 8, 9, 10, 15, 20, 25, 30, 35, 40, 45 or 50% of the volume of the cell culture prior to providing the supplementary components.

The cell culture can be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc. For example, pH can be controlled by supplying an appropriate amount of acid or base and oxygenation can be controlled with sparging devices that are well known in the art.

In certain embodiments of the present invention, the practitioner can find it beneficial or necessary to periodically monitor particular conditions of the growing cell culture. Monitoring cell culture conditions allows the practitioner to determine whether the cell culture is producing recombinant polypeptide or protein at suboptimal levels or whether the culture is about to enter into a suboptimal production phase.

In order to monitor certain cell culture conditions, it will be necessary to remove small aliquots of the culture for analysis. One of ordinary skill in the art will understand that such removal can potentially introduce contamination into the cell culture, and will take appropriate care to minimize the risk of such contamination.

As non-limiting example, it can be beneficial or necessary to monitor temperature, pH, cell density, cell viability, integrated viable cell density, lactate levels, ammonium levels, osmolarity, or titer of the expressed polypeptide or protein. Numerous techniques are well known in the art that will allow one of ordinary skill in the art to measure these conditions. For example, cell density can be measured using a hemocytometer, a Coulter counter, or Cell density examination (CEDEX). Viable cell density can be determined by staining a culture sample with Trypan blue. Since only dead cells take up the Trypan blue, viable cell density can be determined by counting the total number of cells, dividing the number of cells that take up the dye by the total number of cells, and taking the reciprocal. HPLC can be used to determine the levels of lactate, ammonium or the expressed polypeptide or protein. Alternatively, the level of the expressed polypeptide or protein can be determined by standard molecular biology techniques such as Coomassie staining of SDS-PAGE gels, Western blotting, Bradford assays, Lowry assays, Biuret assays, and UV absorbance. It can also be beneficial or necessary to monitor the post-translational modifications of the expressed polypeptide or protein, including phosphorylation and glycosylation.

The practitioner can also monitor the metabolic status of the cell culture, for example, by monitoring the glucose, lactate, ammonium, and amino acid concentrations in the cell culture, as well as by monitoring the oxygen production or carbon dioxide production of the cell culture. For example, cell culture conditions can be analyzed by using NOVA Bioprofile 100 or 400 (NOVA Biomedical, Wash.). Additionally, the practitioner can monitor the metabolic state of the cell culture by monitoring the activity of mitochondria. In embodiment, mitochondrial activity can be monitored by monitoring the mitochondrial membrane potential using Rhodamine 123. Johnson et al., 1980. *P.N.A.S.* 77(2):990-994.

Isolation of Expressed Polypeptide

In general, it will typically be desirable to isolate and/or purify proteins or polypeptides expressed according to the present invention. In one embodiment, the expressed polypeptide or protein is secreted into the medium and thus cells and other solids can be removed, as by centrifugation or filtering for example, as a first step in the purification process.

Alternatively, the expressed polypeptide can be bound to the surface of the host cell. In this embodiment, the media is removed and the host cells expressing the polypeptide or protein are lysed as a first step in the purification process. Lysis of mammalian host cells can be achieved by any number of means well known to those of ordinary skill in the art, including physical disruption by glass beads and exposure to high pH conditions.

The polypeptide can be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, (eds.), *Protein Expression: A Practical Approach*, Oxford Univ. Press, 1999; and Deutscher, M, P., Simon, M. I., Abelson, J. N. (eds.). Guide to Protein Purification: Meth. Enzymol. 182), Academic Press, 1997, all incorporated herein by reference. For immunoaffinity chromatography in particular, the protein can be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin can be added at any or all stages in order to reduce or eliminate degradation of the polypeptide or protein during the purification process. Protease inhibitors are particularly desired when cells must be lysed in order to isolate and purify the expressed polypeptide or protein. One of ordinary skill in the art will appreciate that the exact purification technique will vary depending on the character of the polypeptide or protein to be purified, the character of the cells from which the polypeptide or protein is expressed, and the composition of the medium in which the cells were grown.

Pharmaceutical Compositions

A polypeptide of therapeutic interest, such as an antibody, or fragment thereof, or virus can be formulated as a pharmaceutical composition for administration to a subject, e.g., to treat or prevent a disorder or disease.

Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents; and the like that arc physiologically compatible. The composition can include a pharmaceutically acceptable salt, e.g., an acid addition salt or a base addition salt (See e.g., Berge, S. M., et al. (1977) *J. Pharm. Sci.* 66:1-19). In one embodiment, a pharmaceutical composition is an immunogenic composition comprising a virus produced in accordance with methods described herein.

Pharmaceutical formulation is a well-established art, and is further described, e.g., in Gennaro (ed.), Remington. *The Science and Practice of Pharmacy,* 20th ed., Lippincott, Williams & Wilkins (2000) (ISBN: 0683306472); Ansel et al., *Pharmaceutical Dosage Forms and Drug Delivery Systems, 7th Ed*., Lippincott Williams & Wilkins Publishers (1999) (ISBN: 0683305727); and Kibbe (ed,), *Handbook of Pharmaceutical. Excipients American Pharmaceutical Association,* 3rd Ed. (2000) (ISBN: 091733096X).

The, pharmaceutical compositions can be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically, compositions for the agents described herein are in the form of injectable or infusible solutions.

In one embodiment, an antibody is formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the polypeptide can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known, See, e.g., *Sustained and Controlled Release Drug Delivery Systems*, J. R. Robinson, ed., Marcel Dekker, Inc., New York (1978).

The foregoing description is to be understood as being representative only and is not intended to be limiting. Alternative methods and materials for implementing the invention and also additional applications will be apparent to one of skill in the art, and are intended to be included within the accompanying claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., Sambrook et al., ed., Cold Spring Harbor Laboratory. Press (1989); *Molecular Cloning: A Laboratory Manual*, Sambrook et al., ed., Cold Springs Harbor Laboratory, New York (1992), *DNA Cloning*, D. N. Glover Volumes I and II (1985); *Oligonucleotide Synthesis*, M. J. Gait ed., (1984); Mullis et al. U.S. Pat. No. 4,683,195*; Nucleic Acid Hybridization*, B. D. Hames & S. J. Higgins eds. (1984); *Transcription and Translation: B*. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, Methods In Enzymology, Academic Press, Inc., N.Y,; *Gene Transfer Vectors for Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology* Volumes-I-IV, D. M, Weir and C. C, Blackwell, eds., (1986); *Manipulating the Mouse Embryo*, Cold Spring Harbor Laboratory Press, Cold Spring Harbor, N.Y., (1986); and in Ausubel et al *Current Protocols in Molecular Biology*, John Wiley and Sons, Baltimore, Md. (1989).

General principles of antibody engineering are set forth in *Antibody Engineering,* 2nd edition, C. A. K. Borrebaeck, Ed., Oxford Univ. Press (1995). General, principles of protein engineering are set forth in *Protein Engineering, A Practical Approach*, Rickwood, D., et al., Eds., IRL Press at Oxford Univ, Press, Oxford, Eng. (1995). General principles of antibodies and antibody-hapten binding are set forth in: Nisonoff, A., *Molecular Immunology,* 2nd ed., Sinauer Associates, Sunderland, Mass. (1984); and Steward, M, W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al., (eds), *Basic and Clinical—Immunology* (8th ed.), Appleton & Lange, Norwalk, Conn. (1994) and Mishell and Shiigi (eds), Selected Methods in Cellular Immunology, W.H. Freeman and Co., New York (1980).

Standard reference works setting forth general principles of immunology include *Current Protocols in Immunology*, John Wiley & Sons, New York; Klein, *J., Immunology: The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevier Amsterdam (1984), *Kuby Immunology* 4th ed, Ed. Richard A. Goldsby, Thomas J. Kindt and Barbara A. Osborne, H. Freemand & Co, (2000); Roitt, I., Brostoff, J. and Male D., Immunology 6th ed, London: Mosby (2001); Abbas A. Abul, A. and Lichtman, A., *Cellular and Molecular Immunology Ed* 5, Elsevier Health Sciences Division (2005); Kontermann and Dubel, *Antibody Engineering*, Springer Verlan (2001); Sambrook and Russell, *Molecular Cloning: A Laboratory Mammal*, Cold Spring Harbor Press (2001); Lewin, Genes VIII, Prentice Hall (2003); Harlow and Lane, *Antibodies; A Laboratory Manual*, Cold Spring Harbor Press (1988); Dieffenbach and Dveksler, *PCR Primer* Cold Spring Harbor Press (2003).

All of the references cited above, as well as all references cited herein, are incorporated herein by reference in their entireties.

Reference will now be made to specific examples illustrating the disclosure. It is to be understood that the examples are provided to illustrate exemplary embodiments and that no limitation to the scope of the disclosure is intended thereby.

EXAMPLES

Example 1

Addition of Dextran Sulfate and Ferric Citrate Maintains Lactate Levels and Decreases Ammonium Production Materials and Methods Cell line: The cell line used in this study produced a neublastin polypeptide. The cell line was constructed using DG44 adapted to grow in serum-free medium (Prentice, 2007).

Culture Medium: Basal and feed medium used for this experiment are both proprietary in-house media that were previously described in Huang, 2010 and Kshirsagar, 2012. Both media are chemically defined. Briefly the basal medium CM3 was used for all, maintenance stages. A modified version of CND, called CM3V2, with additional ferric citrate and dextran sulfate, was used for the production stage. This medium contains glucose, amino acids, vitamins, minerals, and trace elements necessary for the robust cultivation of mammalian cells. Feed medium, is a more concentrated version of the basal medium with the nutritional content optimized to maximize growth and productivity. No lactate is present in the feed medium. Again citrate is included in the feed medium as a chelating agent but is present in feed medium at 2,4 InM citrate. Both the basal medium and the feed medium comprised ferric citrate, Dextran sulfate was included in feed medium between 0-10 g/L dextran sulfate.

Cell culture methods: Cells were thawed and maintained as in a previous report (Kshirsagar, et al. 2012 *Biotechnol. Bioeng*. Huang, et al., *Biotechnol. Prog* 26(5):1400-1410 (2010)). Basal medium for thaw and passing was the same as in previous reports (Kshirsagar/Huang). Briefly, cells were thawed and maintained in 3 L shake flasks (Corning Life Sciences, Corning, N.Y.) with 1 L working volumes and were passaged every 2 days. For maintenance cultures the incubator was Set at 36° C. and 5% $CO_2$.

Bioreactor culture conditions: Fed batch cultures were performed in S L glass Applikon vessels using Finesse TruBio DV controllers (Finesse Solutions, San Jose, Calif.) with an initial working volume between 2-2.5 L. Bioreaators were seeded at constant seed density of 4×105 cells/ml. Concentrated feed medium was delivered on days 3, 5, and every day following through harvest. Temperature was maintained at 36° C. and pH was controlled at 7.1+/−0.2 by the addition of either 1 M sodium carbonate or carbon dioxide. Dissolved oxygen was maintained at 30% by air and oxygen sparge using a drilled hole sparger. Agitation was maintained between 200-400 RPM throughout the culture to limit total gas flow, while an overlay was maintained between 0.005 and 0.04 vvm.

Offline analysis: Samples were taken on mast days and analyzed with a variety of equipment. Cell density and viability were measured using the standard technique of trypan blue exclusion using a Cedex (Roche Innovatis AG, Germany), Glucose, lactate, ammonium, potassium and sodium data were collected using a NOVA Bioprofile 100 or 400 (NOVA Biomedical, Wash.).

In order to investigate the effect of dextran sulfate and ferric citrate on the lactate and the ammonium levels in cell culture, 0.25 g/L dextran sulfate and 2.3 mM ferric citrate were added to the production medium on clay 0. In some cases, no additional dextran sulfate is provided. In some cases, additional dextran sulfate is added via the feed.

In 902 using CM3 basal medium, lactate levels started at about 0.5 g/L on day 0, peaked at about 2-2.5 g/L on day 3, and then rapidly decreased to about 0.5 g/L from day 10 to day 14 (FIG. 1A), Lactate levels then slightly increased again and remained at about 0.5-1/L between day 15 and day 17, In the presence of dextran sulfate and ferric citrate. using CM3v2 basal medium, lactate level in the 902 medium was well maintained at about 2-2.5 g/L between day 3 and day 9, then decreased eventually to about 1 g/L on day 17 (FIG. 1A). Similarly, lactate level in N65 culture using CM3 basal medium peaked at about 2.5 g/L on day 5, then rapidly decreased to about 1 gE, on day 14, However, the presence of dextran sulfate and ferric citrate almost sustained the lactate level in the N65 medium at about 2.5-3 g/L between day 5 and day 17, with only a very slight decrease from day 7 to day 16 (FIG. 1A).

Figure 1B:
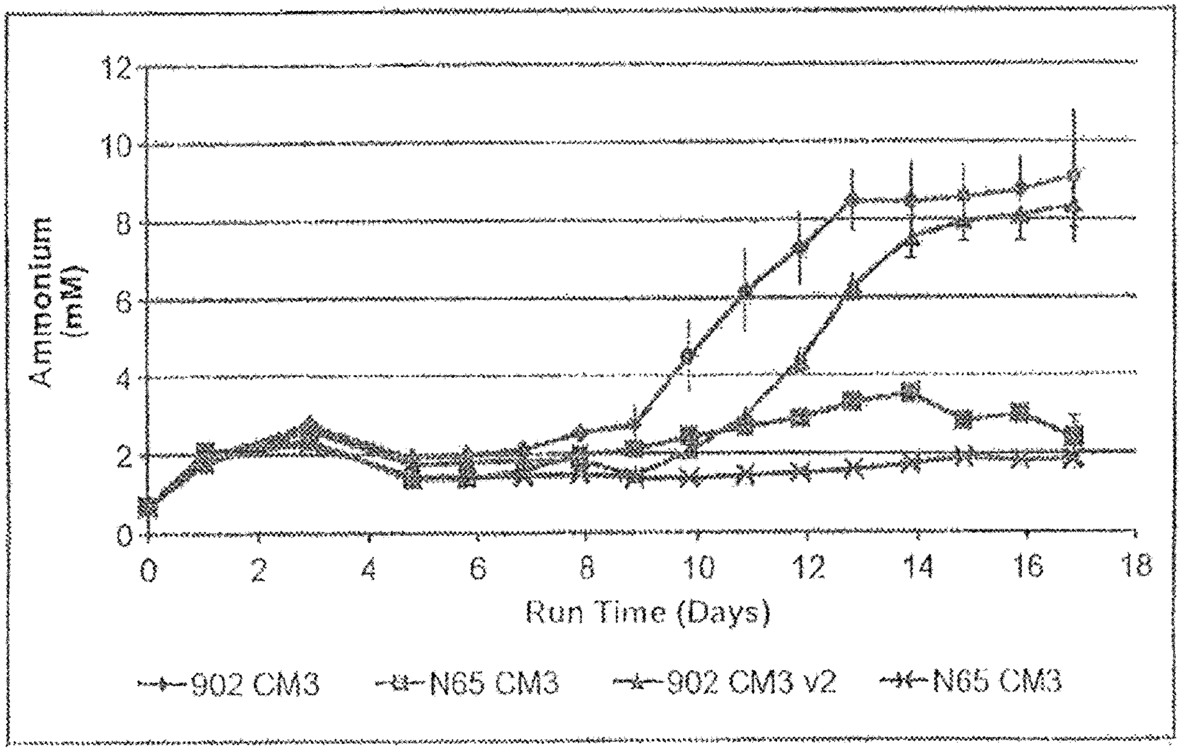

Ammonium leveEq in the cell culture started at about 0.5 mivi on day 0 in medium with or without dextran sulfate or ferric citrate (FIG. 1B), In 902, using CM3 basal medium, the ammonium level slightly increased to about 3 mM on day 9, then dramatically climbed up to about 8 mM on day 13, and reached about 9 mM on day 17. In the presence of dextran sulfate and ferric citrate, the ammonium production in the 902 medium was significantly reduced from day 0 to day 17, with between about 1 g/L and about 3 g/L ammonium reduction from day 9 to day 14 (FIG. 1B). In N65 using 0/13 basal medium, the ammonium level increased from 0.5 mM to nearly 4 mM on day 14, then slightly decreased to about 2 mM on day 17. In the presence of dextran sulfate and ferric citrate, the ammonium production in the N65 medium was well maintained at or below 2 niM from day 0 to day 17 (FIG. 1B).

Therefore, the addition of dextran sulfate and ferric citrate is able to maintain lactate levels and decrease ammonium production in cell culture.

Example 2

Figure 2A:
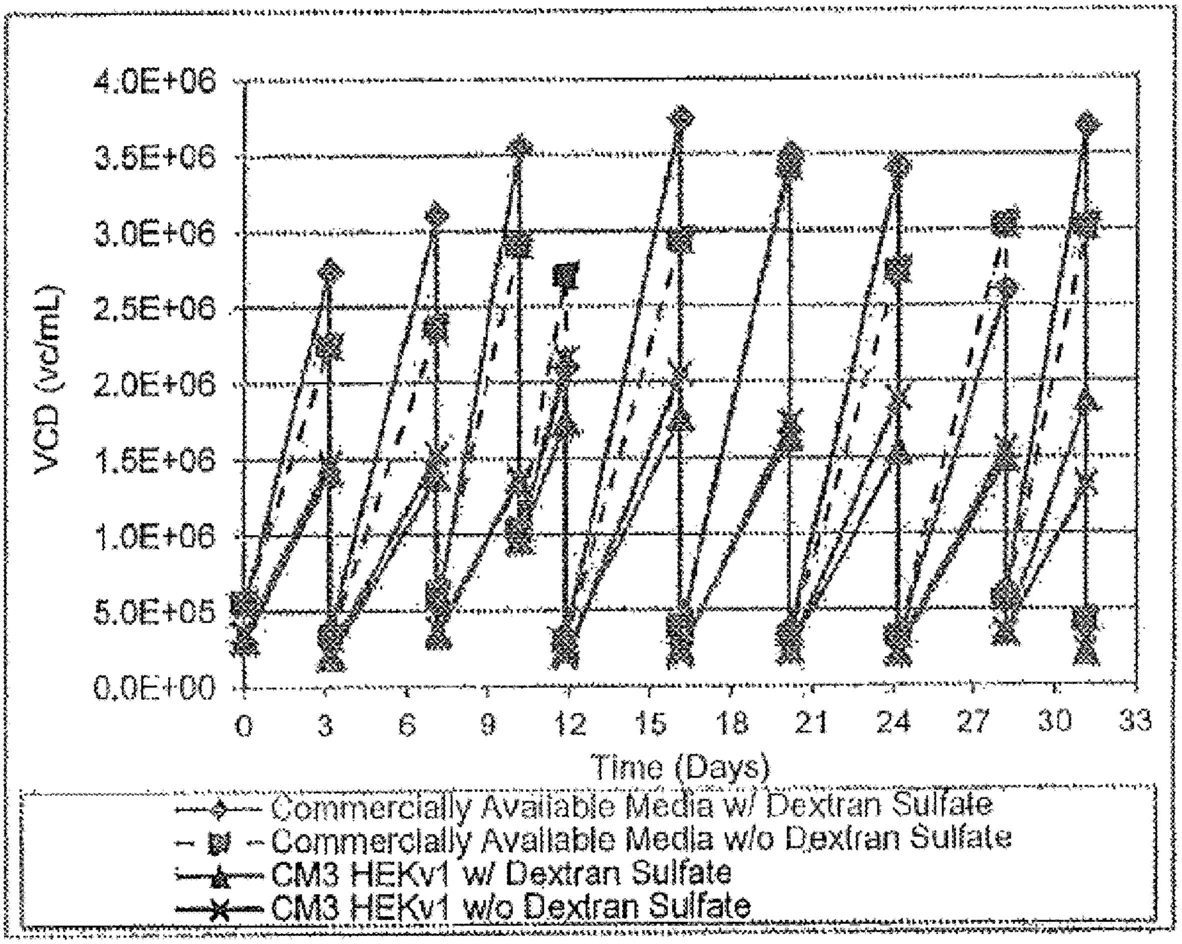
FIG. 2A-2B are graphic representations of the VC/ML (A) and viability (B) after addition of dextran sulfate to shaker flasks.
Figure 2B:
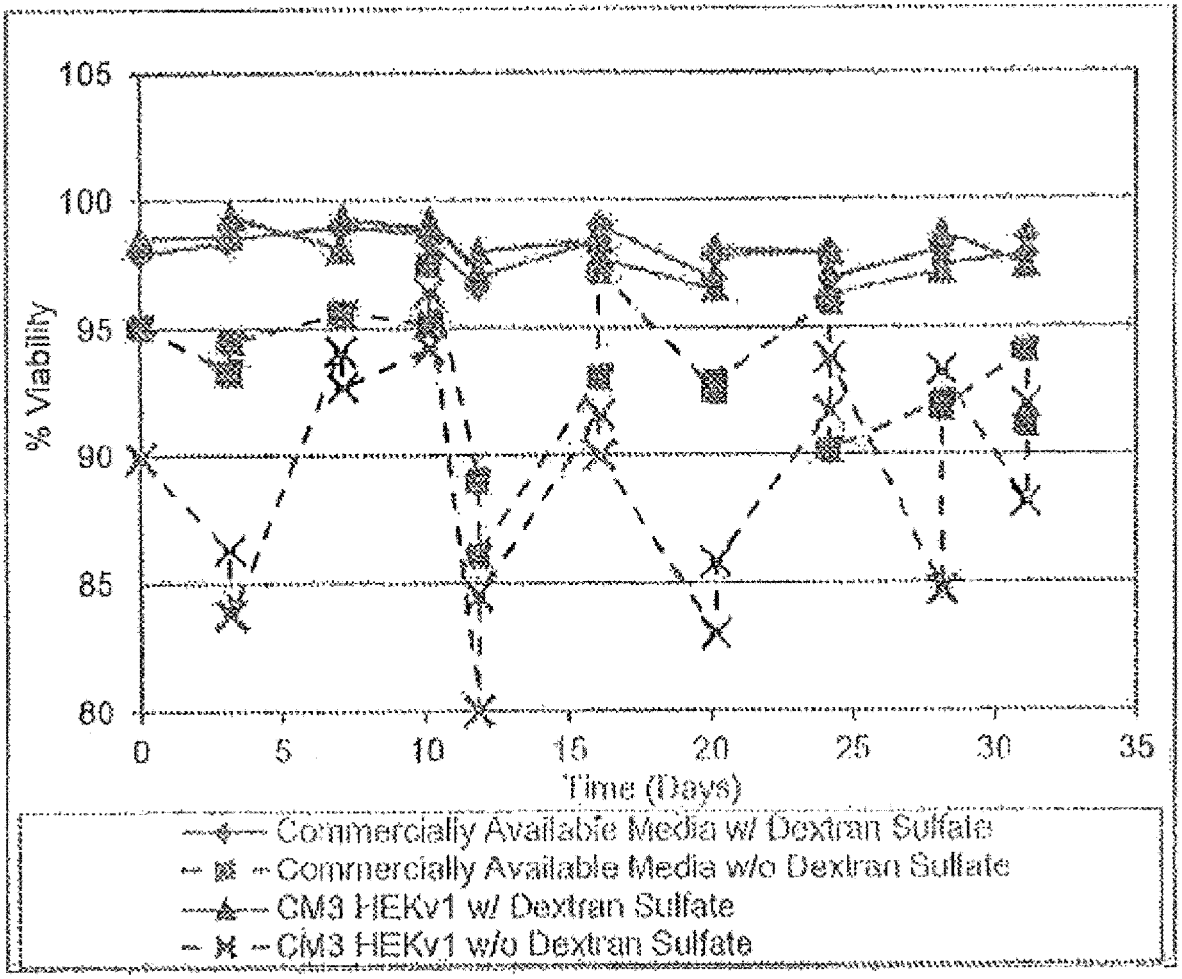

Addition of Dextran Sulfate Stabilizes Viability of Shake Flask Maintenance Culture To investigate the effect of dextran sulfate on the viability of shake flask maintenance culture, 0.1 g/L. dextran sulfate was added to a commercially available medium lacking dextran sulfate and CM3 HEKv1, a rebalanced version of CM3 optimized for FIEK293 culture. While the viable cell density in medium comprising 0.1 g/L dextran sulfate was comparable to that in medium with no dextran sulfate (FIG. 2A); the presence of dextran sulfate greatly increased the percentage of viable cells (FIG. 2B). Cell viability in maintenance culture without dextran sulfate went through frequent sudden decreases from day 0 to clay 32 and varied dramatically between about 80% to about 95%, but the presence of 0.1 g/L dextran sulfate effectively maintained, the percentage of cell viability above 95% at all the time points (FIG. 2B). Therefore, addition of dextran sulfate is able to stabilize viability of shake flask maintenance culture.

Cell line: The cell line used in this study produced a Factor VIII polypeptide. The cell line was constructed using HEK 293 adapted to grow in serum-free medium.

Culture medium: Basal and feed medium used for this experiment are both modified versions of proprietary inhouse media that were previously described in Huang (2010) and Kshirsagar (2012) with rebalanced amino acid and salt concentrations and named CM3.1-.ILK.y1. Both media are chemically defined. Briefly. the basal medium, CM3 I-IEKv I. was used for all maintenance stages unless otherwise noted. A modified version of CM3 HEKv1, supplemented with dextran sulfate, was used for direct compulsion in both Maintenance and production culture. This medium contains glucose, amino acids, vitamins, minerals, and trace elements necessary for the robust cultivation of mammalian cells, Feed medium is a more concentrated version of the basal medium with the nutritional content optimized to maximize growth and productivity. No lactate is present in the feed medium. Dextran sulfate was not included in feed medium.

Cell culture methods: Cells were thawed and maintained as in a previous report (Kshirsagar, et al, 2012 *Biotechnol. Bioeng*. Huang, et al, *Biotechnology. Progress* 26(5): 1400-1410 (2010)), Basal medium for thaw and passing, CM3 HEKv1, was a modified version as that used in previous reports with rebalanced amino acid and salt concentrations (Kshirsagar/Huang) Briefly, cells were thawed and maintained in 1 L shake flasks (Corning Life Sciences, Corning, N.Y.) with 0.2 L working volumes and were passaged every 2-3 days. For maintenance cultures the incubator was controlled at 37° C. and 10% $CO_2$.

Offline analysis: Samples were taken on most days and analyzed with a variety of equipment. Cell density and viability were measured using the standard technique of trypan blue exclusion using a Cedex (Roche Imiovatis AG, Germany). Glucose, lactate, ammonium, potassium, and sodium data were collected using a NOVA Bioprofile 100 or 400 (NOVA Biomedical, Wash.).

Example 3

Figure 3A:
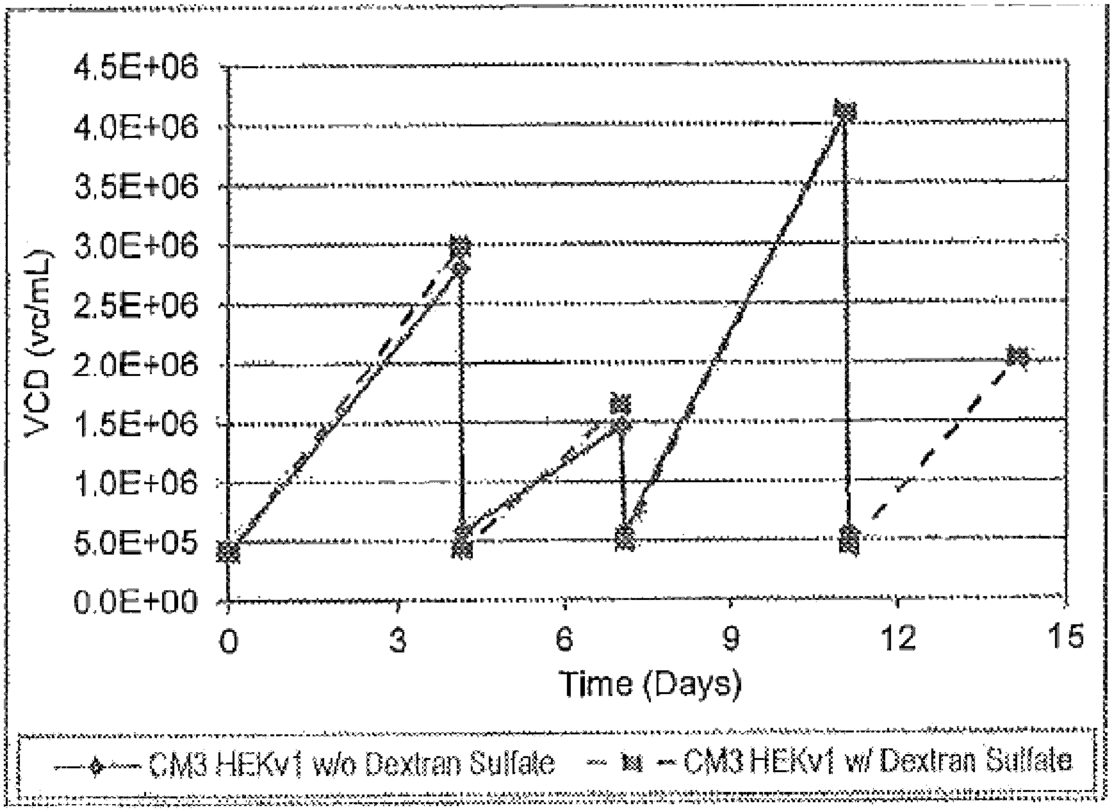
FIG. 3A-3B are graphic representations of the VCD (A) and viability of cultures after the addition of dextran sulfate to the bioreactor inoculum train culture.
Figure 3B:
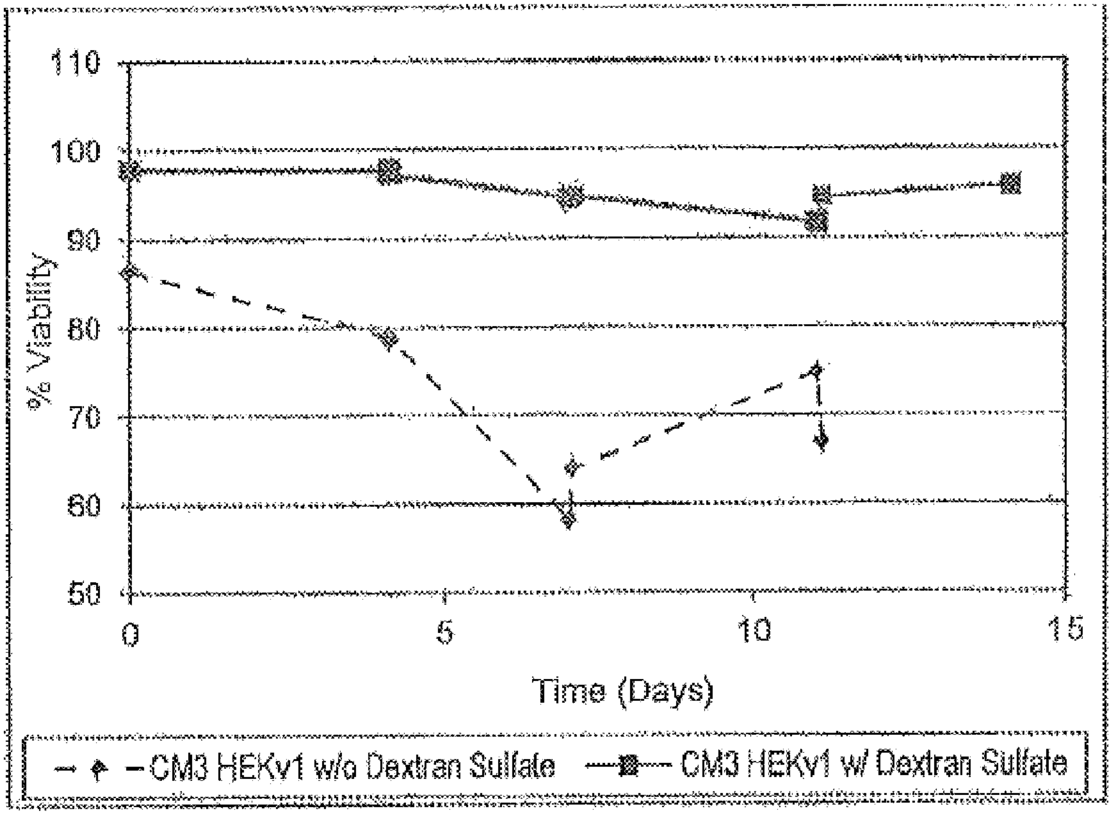

Addition of Dextran Sulfate Stabilizes Viability of Bioreactor Inoculum Train Culture To investigate the effect of dextran sulfate on the viability of bioreactor inoculum train culture, 0.1 g/L dextran sulfate was added to CM3 HEKv1 on day 0. While the presence of dextran sulfate did not affect the viable cell density (FIG. 3A), it effectively maintained the percentage of viable cells in the bioreactor inoculum train culture (FIG. 3B), Cell viability in inoculum train culture without dextran sulfate dropped from about 85% on day 0 to below 60% on day 7, and was between about 60% and about 75% after day 7, but addition of 0.1 g/L dextran sulfate effectively maintained the percentage of cell viability at about 95% at all the time points 3B). Therefore, addition of dextran sulfate is able to stabilize viability of bioreactor inoculum train culture.

Bioreactor culture conditions: Fed batch cultures were performed M 5 L glass Applikon vessels using Finesse TruBio DV controllers (Finesse Solutions, San Jose, Calif.) with an initial working volume between 2-2.5 L. Bioreactors were seeded at constant seed density of 4×10 cells/mi. Temperature was maintained at 37° C. and pH was controlled at 7.0.11-0.3 by the addition of either 1 M sodium carbonate or carbon dioxide, Dissolved oxygen was maintained at 50% by air and oxygen sparge using a drilled hole sparger. Agitation was maintained at 125 RPM throughout the culture to limit total gas flow, while an overlay was maintained between 0.005 and 0.04 vvm.

Example 4

Figure 4A:
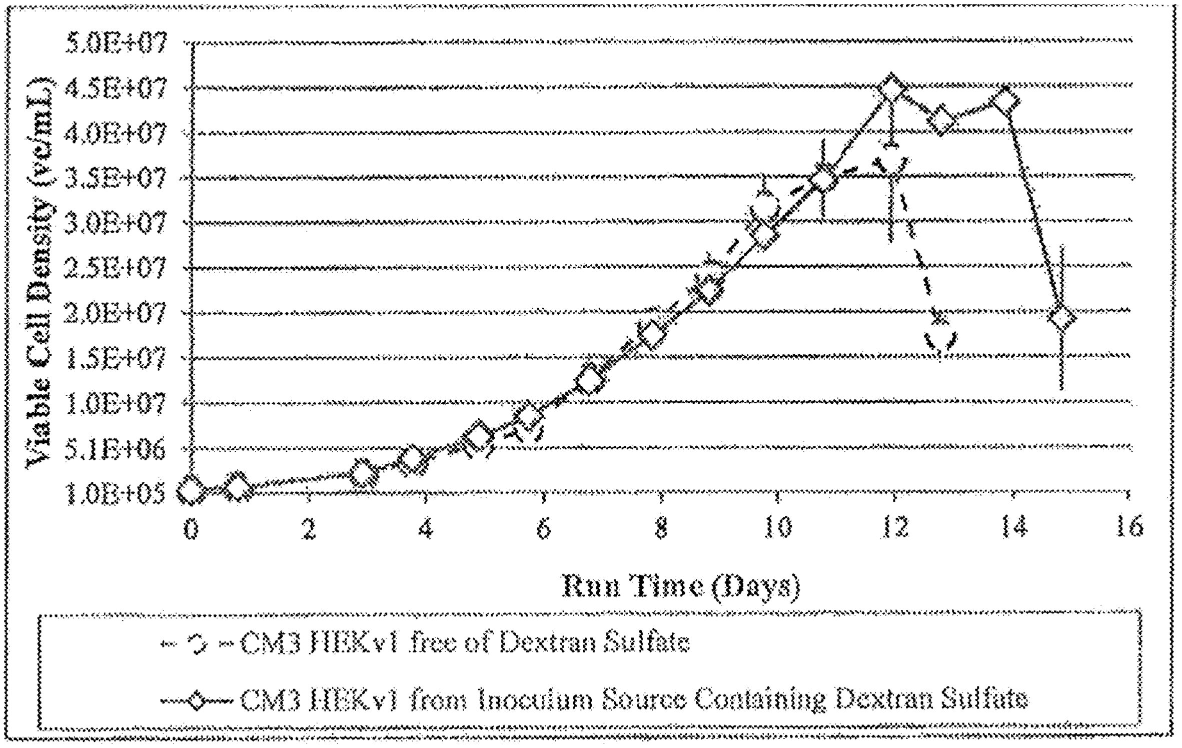
FIG. 4A-4B are graphic representations of viable cell density (A) and the viability (B) of cell cultures in production bioreactors inoculated using dextran sulfate.
Figure 4B:
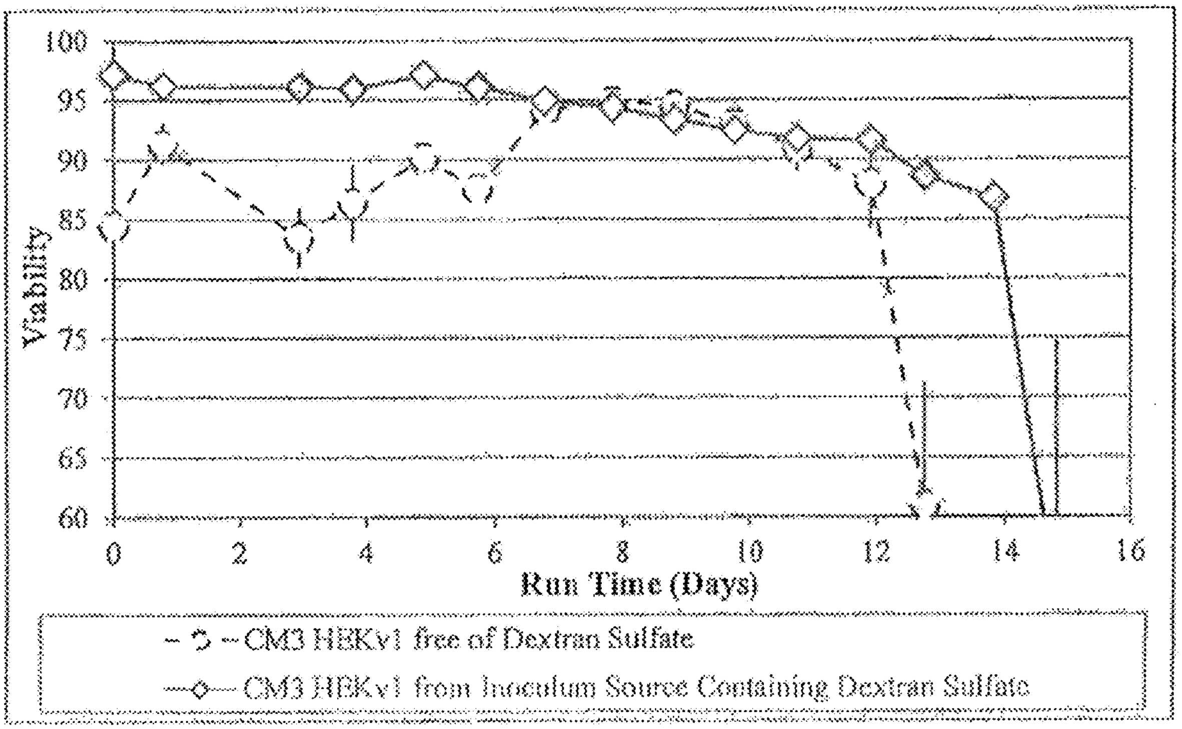

Dextran Sulfate Containing Inoculum was Enough to Stabilize Early Stage Culture Viability in Production Bioreactors To further investigate whether the amount of dextran sulfate contained in the inoculum culture was able to stabilize cell viability in production bioreactors, bioreactor culture was inoculated with inoculum culture containing 0.1 g/L dextran sulfate on day 0, and no additional dextran sulfate was added in subsequent feed medium, The presence of dextran sulfate in the production bioreactor culture was able to stabilize both viable cell density and cell viability for two more days (FIGS. 4A-4B). In bioreactor culture without dextran sulfate, both viable cell density and cell viability sharply decreased after day 12, but the presence of dextran sulfate postponed this decrease to day 14 (FIG. 4B). In addition, the presence of dextran sulfate also greatly maintained the cell viability above 95% from day 0 to day 6, when the viability in dextran sulfate free culture varied between 80% to about 90% (FIG. 4B). Therefore, inoculation of production culture using dextran sulfate containing inoculum is enough to stabilize early stage culture viability.

Bioreactor culture conditions: Fed batch cultures were performed in 5 L glass Applikon vessels using Finesse TruBio DV controllers (Finesse Solutions, San Jose, Calif.) with an initial working volume between 2-2.5 L. Bioreactors were seeded at constant seed density. of $5\times10^5$ cells/ml. Concentrated feed medium was delivered on day 3, and every day following through harvest. Temperature was maintained at 35.5° C. and pH was controlled at 7.2+1-0.1 by the addition of either 1 M sodium carbonate or carbon dioxide. Dissolved oxygen was maintained at 30% by air and oxygen sparge using a drilled hole sparger. Agitation was maintained between 200-400 RPM throughout the culture to limit total gas flow, while an overlay was maintained between 0.005 and 0.04 vvm.

Offline analysis: Samples were taken on most days and analyzed with a variety of equipment. Cell density and viability were measured using the standard technique of trypan blue exclusion using a Cedex (Roche Innovatis AG, Germany). Glucose, lactate, ammonium, potassium and sodium data were collected using a NOVA Bioprofile 100 or 400 (NOVA Biomedical, Wash.).

Example 5

Production of Neublastin Antibody in CHO Cell Cultures

The DNA encoding the heavy and light chains of the murine IgG1 anti-neublastin monoclonal antibody (FIG. 8) was cloned into a eukaryotic expression vector plasmid bXLTBR.9 containing the cytomegalovirus (CMV) intermediate early promoter (pGV90). Cloning was followed by transfection of the P3B3-containing plasmid into dihydrofolate reductase (DHFR)-deficient DG44i Chinese hamster ovary (CHO) host cells (Cell Line Ref: 13805-32 (Thermo Fisher, Waltham, Mass.) (Urlaub and Chasin (1980) *P.N.A.S* 77:4216-4221) using the FuGene 6 transfection reagent (Roche Applied Sciences, Indianapolis Ind.).

The anti-neublastin mAb-producing clonal cell line (EAG2659/2660 Clone 8 DG44i) was identified by iterative screening of transfected cells for high specific productivity by flow-assisted cell sorting (FACS) using an anti-human IgG1 monoclonal antibody (Brezinsky et al., (2003).

This cell line was grown in a neomycin selection medium containing 40 μg/ml G418 (gentamicin, Thermo Fisher) or in a growth medium suitable for CHO cell culture (e.g., in shaker flasks at 36.5° C. with 5% $CO_2$. When cell densities reached $3\times10^6$ and $4\times10^6$ cells/ml, cells were transferred to a production vessel seeded with $2\times10^5$ cells/ml and gown at 36.5° C. in 50% atmosphere in dissolved oxygen, with a pH set to 7.4. On day 3, with a density of $2\times10^5$ cells/ml, the vessel was fed with 5% starting culture volume. On day 5, with a density of $4\times10^6$-$5\times10^6$ cells/ml, the temperature was dropped to 28° C. Cells were harvested by centrifugation when the viable cell density had dropped to about 88% (day 18). The conditioned medium was centrifuges at over 1000 g for 20 min and then filtered through a 0.2 μm filter to remove cells and to clarify. The clarified medium was then concentrated about 6× on a Prescale tangential flow 6 $ft^2$ 30 k mol. wt. cutoff cartridge (Millipore, Burington, Mass.). The concentrate supernatant can be stored for over 1 year at −80° C.

Figure 6:
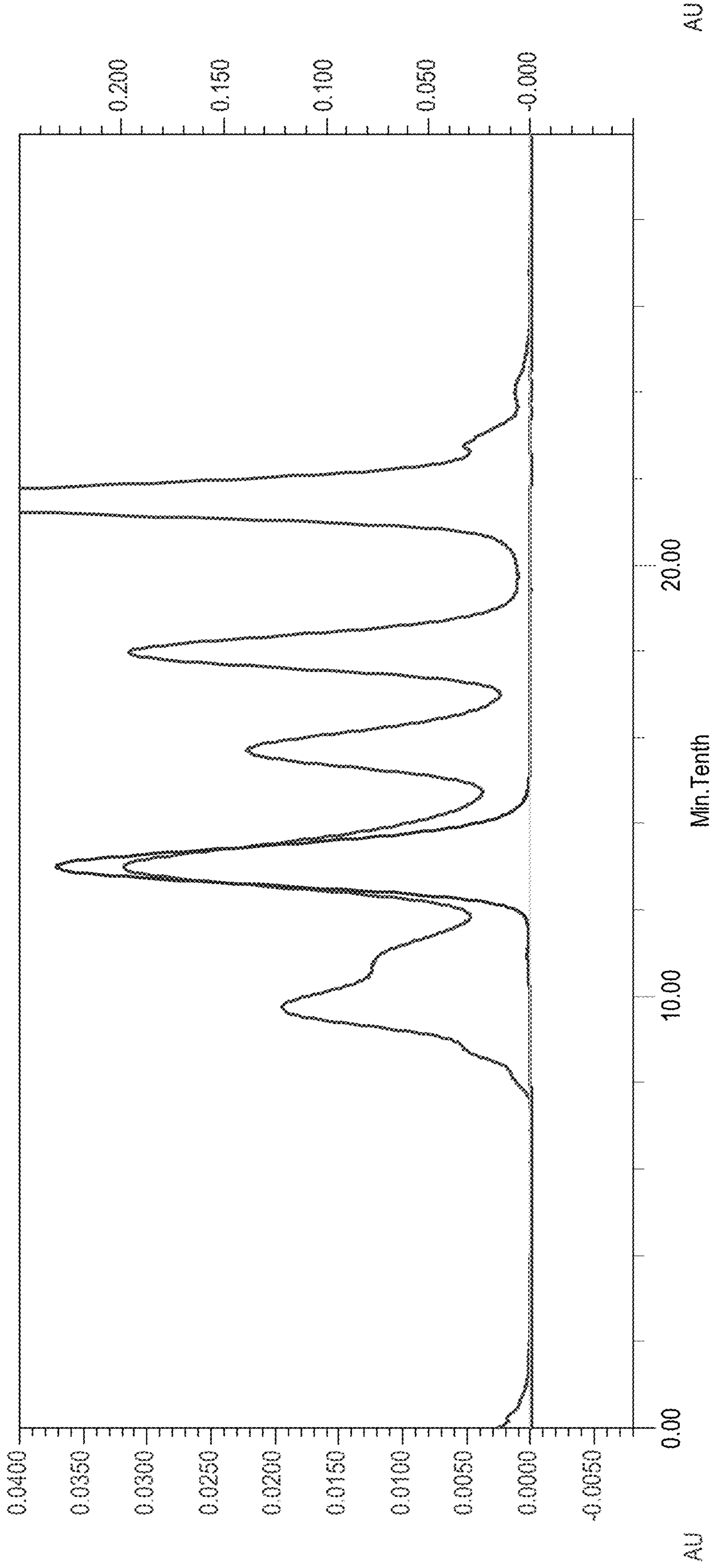
FIG. 6 is a representation of a representation elusion profile of neublastin antibody on a size exclusion chromatography (SEC) column.
Figure 7:
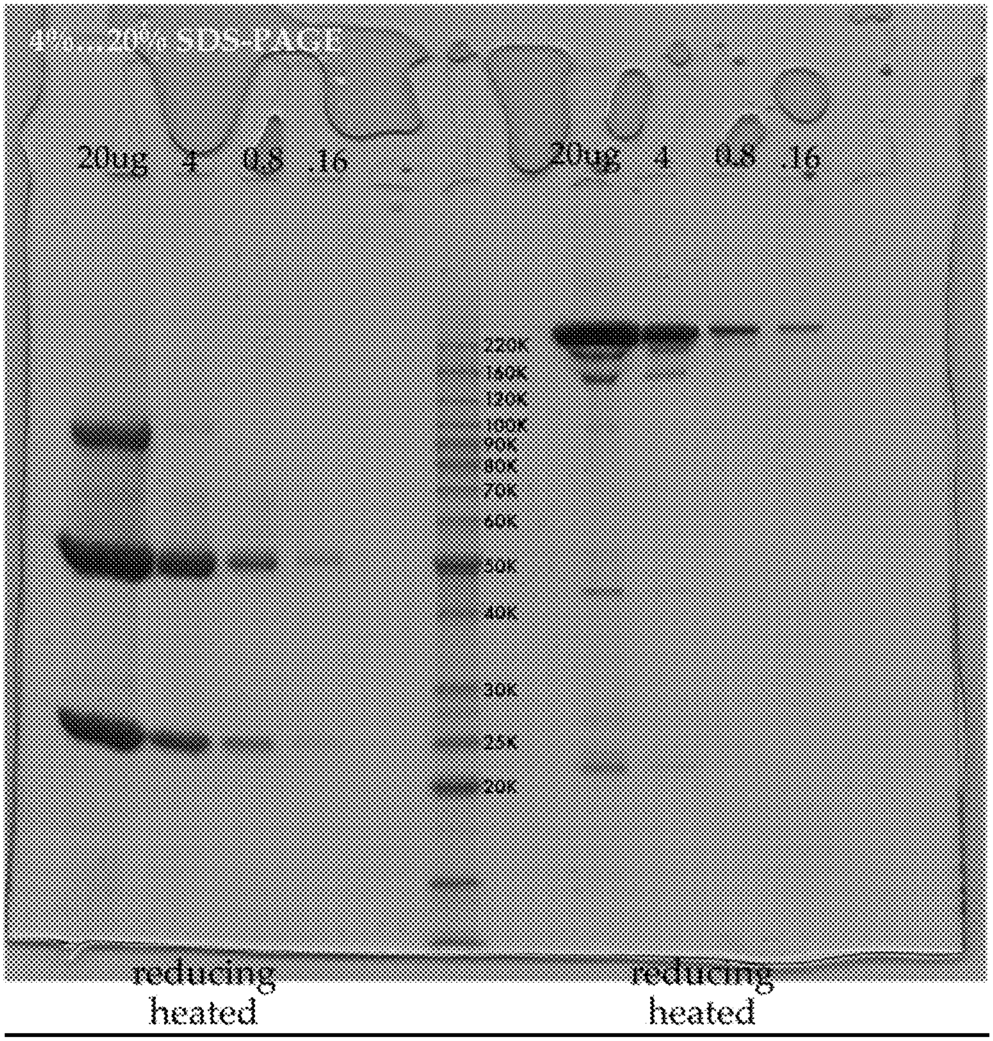
FIG. 7 is a representation of a polyacrylamide gel of the peak material from the SEC column shown in FIG. 6.

The concentrated cell supernatant was brought to 3 M NaCl/1.5 M glycine, pH 8.9 (Single Stranded DNA (SS) Binding Buffer, Thermo Fisher Scientific) and loaded onto an recombinant Protein A Sepharose (recProA Seph) 4FF column (G.E. Lifesciences, Chicago, Ill.). The column was washed with about 7 column volumes (CV) of SS Binding Buffer at 5 CV of 3 M NaCl/25 mM $NaPO_4$, pH 8.6. The protein was then eluded off the column with about 3.5 CV of 2 mm $NaPO_4$/100 mM NaCl, pH 2.8. The pooled eluate was then dialyzed into 20 CV of PBS (20 mM $NaPO_4$/50 mM NaCl, pH 7.1) four times for a minimum of 8 hr each time. After dialysis, the material was 0.2 μm sterile-filtered and analyzed by size exclusion chromatography (SEC) on a Superdex200 (GE Healthcare Life Sciences, Chicago, Ill.) (1 cm×20 cm). FIG. 6 shows that the antibody (P3B3) eluted as an 158 k peak. The peak material was run on 4%-20% SDS-PAGE (FIG. 7) and tested for endotoxin. The amino acid sequence of the heavy (SEQ ID NO:2) and light (SEQ ID NO:4) chains of the antibody are shown in FIGS. 5B-5D.

EQUIVALENTS

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and, described herein will become apparent to those skilled in the art from the foregoing description and accompanying drawings. Such modifications are intended to fall within the scope of the appended claims.

What is claimed is:

1. A cell culture comprising a mammalian cell line genetically modified to express, and which expresses, a neublastin antibody polypeptide, or a fragment thereof, in a cell culture medium, wherein the neublastin antibody polypeptide comprises:

three heavy chain complementarity determining regions (HCDRs), wherein HCDR1 comprises amino acid residues 27 to 35 of SEQ ID NO:2, HCDR2 comprises amino acid residues 47 to 61 of SEQ ID NO:2, and HCDR3 comprises amino acid residues 97 to 111 of SEQ ID NO:2, and three light chain complementarity determining regions (LCDRs), wherein LCDR1 comprises amino acid residues 27 to 34 of SEQ ID NO:4, LCDR2 comprises amino acid residues 46 to 56 of SEQ ID NO:4, and LCDR3 comprises amino acid residues 89 to 96 of SEQ ID NO:4.

2. The cell culture of claim 1, wherein the neublastin antibody polypeptide comprises SEQ ID NO: 2, or a fragment thereof.

3. The cell culture of claim 1, wherein the neublastin antibody polypeptide comprises SEQ ID NO: 4, or a fragment thereof.

4. The cell culture of claim 1, wherein the neublastin antibody polypeptide comprises SEQ ID NO: 4, or a fragment thereof, and wherein the neublastin antibody polypeptide comprises SEQ ID NO: 2, or a fragment thereof.

5. The cell culture of claim 1, wherein the mammalian cell line is a Chinese Hamster Ovary (CHO) cell line.

6. The mammalian cell culture of claim 1, wherein the cells have been adapted to grow in a serum-free medium, an animal protein-free medium, or a chemically defined medium.

7. The cell culture of claim 1, wherein the mammalian cells have been genetically modified with a polynucleotide encoding the neublastin antibody polypeptide, or a fragment thereof.

8. The mammalian cell culture of claim 1, wherein the culture is a perfusion culture or is a fed batch culture.

9. The mammalian cell culture of claim 1, wherein the medium is a serum-free medium, AN animal protein-free medium, or a chemically defined medium.

10. A neublastin antibody polypeptide produced in a large-scale mammalian cell culture, the culture comprising mammalian cells genetically modified to express, and which express, the neublastin antibody polypeptide, or a fragment thereto, in a mammalian cell culture, wherein the neublastin antibody polypeptide comprises:

three heavy chain complementarity determining regions (HCDRs), wherein HCDR1 comprises amino acid residues 27 to 35 of SEQ ID NO:2, HCDR2 comprises amino acid residues 47 to 61 of SEQ ID NO:2, and HCDR3 comprises amino acid residues 97 to 111 of SEQ ID NO:2, and three light chain complementarity determining regions (LCDRs), wherein LCDR1 comprises amino acid residues 27 to 34 of SEQ ID NO:4, LCDR2 comprises amino acid residues 46 to 56 of SEQ ID NO:4, and LCDR3 comprises amino acid residues 89 to 96 of SEQ ID NO:4.

11. The neublastin antibody polypeptide of claim 10, comprising a heavy chain polypeptide comprising SEQ ID NO: 2, or a fragment thereof.

12. The neublastin antibody polypeptide of claim 10, comprising a light chain polypeptide comprising SEQ ID NO: 4, or a fragment thereof.

13. The neublastin antibody polypeptide of claim 10, comprising a light chain polypeptide comprising SEQ ID NO: 4, or a fragment thereof, and a heavy chain polypeptide comprising SEQ ID NO: 2, or a fragment thereof.

14. The neublastin antibody polypeptide of claim 10, wherein the mammalian cell culture comprises CHO cells expressing the neublastin antibody polypeptide, or a fragment thereof.

15. The neublastin antibody polypeptide of claim 10, wherein the cells have been adapted to grow in serum-free medium, an animal protein-free medium, or a chemically defined medium.

16. The neublastin antibody polypeptide, or fragment thereof, of claim 10, which has been isolated from the mammalian cell culture.

17. A pharmaceutical formulation comprising the neublastin antibody of claim 16 in a pharmaceutically acceptable carrier.

* * * * *

SEQUENCE LISTING

```
<160> NUMBER OF SEQ ID NOS: 12

<210> SEQ ID NO 1
<211> LENGTH: 465
<212> TYPE: PRT
<213> ORGANISM: Mus musculus

<400> SEQUENCE: 1

Met Asp Ser Arg Leu Asn Leu Val Phe Leu Val Leu Val Leu Lys Gly
1               5                   10                  15

Val Leu Cys Glu Val Lys Val Val Glu Ser Gly Gly Gly Leu Val Arg
            20                  25                  30

Pro Gly Gly Ser Leu Lys Leu Ser Cys Ser Ala Ser Gly Phe Thr Phe
        35                  40                  45

Ser Ser Tyr Ala Met Ser Trp Val Arg Gln Thr Pro Glu Lys Arg Leu
    50                  55                  60

Glu Trp Val Ala Tyr Ile Ser His Gly Gly Gly Asp Thr Tyr Tyr Leu
65                  70                  75                  80
```

-continued

```
Asp Thr Val Lys Gly Arg Phe Thr Ile Ser Arg Asp Asn Ala Lys Asn
                85                  90                  95

Ser Leu Tyr Leu Gln Met Ser Ser Leu Met Ser Glu Asp Thr Ala Met
            100                 105                 110

Tyr Tyr Cys Val Arg Arg Gly Tyr Asp Tyr Asp Gly Asp Tyr Ala Met
        115                 120                 125

Asp Tyr Trp Gly Gln Gly Thr Ser Val Thr Val Ser Ser Ala Lys Thr
    130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Glu Thr Val Thr Cys Asn
    210                 215                 220

Val Ala His Pro Ala Ser Ser Thr Lys Val Asp Lys Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys Val Val Val Asp Ile Ser Lys Asp Asp
        275                 280                 285

Pro Glu Val Gln Phe Ser Trp Phe Val Asp Asp Val Glu Val His Thr
    290                 295                 300

Ala Gln Thr Gln Pro Arg Glu Glu Gln Phe Asn Ser Thr Phe Arg Ser
305                 310                 315                 320

Val Ser Glu Leu Pro Ile Met His Gln Asp Trp Leu Asn Gly Lys Glu
                325                 330                 335

Phe Lys Cys Arg Val Asn Ser Ala Ala Phe Pro Ala Pro Ile Glu Lys
            340                 345                 350

Thr Ile Ser Lys Thr Lys Gly Arg Pro Lys Ala Pro Gln Val Tyr Thr
        355                 360                 365

Ile Pro Pro Pro Lys Glu Gln Met Ala Lys Asp Lys Val Ser Leu Thr
    370                 375                 380

Cys Met Ile Thr Asp Phe Phe Pro Glu Asp Ile Thr Val Glu Trp Gln
385                 390                 395                 400

Trp Asn Gly Gln Pro Ala Glu Asn Tyr Lys Asn Thr Gln Pro Ile Met
                405                 410                 415

Asp Thr Asp Gly Ser Tyr Phe Val Tyr Ser Lys Leu Asn Val Gln Lys
            420                 425                 430

Ser Asn Trp Glu Ala Gly Asn Thr Phe Thr Cys Ser Val Leu His Glu
        435                 440                 445

Gly Leu His Asn His His Thr Glu Lys Ser Leu Ser His Ser Pro Gly
    450                 455                 460

Lys
465

<210> SEQ ID NO 2
<211> LENGTH: 446
```

<212> TYPE: PRT
<213> ORGANISM: Mus musculus

<400> SEQUENCE: 2

```
Glu Val Lys Val Val Glu Ser Gly Gly Gly Leu Val Arg Pro Gly Gly
1               5                   10                  15

Ser Leu Lys Leu Ser Cys Ser Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Tyr Ile Ser His Gly Gly Gly Asp Thr Tyr Tyr Leu Asp Thr Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Met Ser Glu Asp Thr Ala Met Tyr Tyr Cys
                85                  90                  95

Val Arg Arg Gly Tyr Asp Tyr Asp Gly Asp Tyr Ala Met Asp Tyr Trp
            100                 105                 110

Gly Gln Gly Thr Ser Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asp Thr Asp
385                 390                 395                 400
```

```
Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445


<210> SEQ ID NO 3
<211> LENGTH: 234
<212> TYPE: PRT
<213> ORGANISM: Mus musculus

<400> SEQUENCE: 3

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Ala Val Ala Trp Phe Gln Gln Lys Pro Gly Gln Ser Pro
    50                  55                  60

Lys Leu Leu Ile Tyr Phe Ala Ser Asn Arg Phe Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Pro Glu Asp Leu Ala Val Tyr Phe Cys Gln Gln Asp Tyr
            100                 105                 110

Asn Ser Pro Phe Thr Phe Gly Ser Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Arg Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230


<210> SEQ ID NO 4
<211> LENGTH: 214
<212> TYPE: PRT
<213> ORGANISM: Mus musculus

<400> SEQUENCE: 4

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Ala
            20                  25                  30

Val Ala Trp Phe Gln Gln Lys Pro Gly Gln Ser Pro Lys Leu Leu Ile
        35                  40                  45
```

```
Tyr Phe Ala Ser Asn Arg Phe Thr Gly Val Pro Asp Arg Phe Thr Gly
    50                  55                  60

Ser Gly Tyr Gly Thr Asp Phe Thr Phe Thr Ile Ser Thr Val Gln Pro
65                  70                  75                  80

Glu Asp Leu Ala Val Tyr Phe Cys Gln Gln Asp Tyr Asn Ser Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Arg Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 5
<211> LENGTH: 1395
<212> TYPE: DNA
<213> ORGANISM: Artificial Sequence
<220> FEATURE:
<223> OTHER INFORMATION: Predicted nucleotide sequence of heavy chain with signal peptide

<400> SEQUENCE: 5

```
atggatagcc gcctgaacct ggtgtttctg gtgctggtgc tgaaaggcgt gctgtgcgaa     60

gtgaaagtgg tggaaagcgg cggcggcctg gtgcgcccgg gcggcagcct gaaactgagc    120

tgcagcgcga gcggctttac ctttagcagc tatgcgatga gctgggtgcg ccagaccccg    180

gaaaaacgcc tggaatgggt ggcgtatatt agccatggcg gcggcgatac ctattatctg    240

gataccgtga aaggccgctt taccattagc cgcgataacg cgaaaaacag cctgtatctg    300

cagatgagca gcctgatgag cgaagatacc gcgatgtatt attgcgtgcg ccgcggctat    360

gattatgatg gcgattatgc gatggattat tggggccagg gcaccagcgt gaccgtgagc    420

agcgcgaaaa ccaccccgcc gagcgtgtat ccgctggcgc cgggcagcgc ggcgcagacc    480

aacagcatgg tgaccctggg ctgcctggtg aaaggctatt ttccggaacc ggtgaccgtg    540

acctggaaca gcggcagcct gagcagcggc gtgcatacct ttccggcggt gctgcagagc    600

gatctgtata ccctgagcag cagcgtgacc gtgccgagca gcacctggcc gagcgaaacc    660

gtgacctgca acgtggcgca tccggcgagc agcaccaaag tggataaaaa aattgtgccg    720

cgcgattgcg gctgcaaacc gtgcatttgc accgtgccgg aagtgagcag cgtgtttatt    780

tttccgccga aaccgaaaga tgtgctgacc attaccctga ccccgaaagt gacctgcgtg    840

gtggtggata ttagcaaaga tgatccggaa gtgcagttta gctggtttgt ggatgatgtg    900

gaagtgcata ccgcgcagac ccagccgcgc gaagaacagt ttaacagcac ctttcgcagc    960

gtgagcgaac tgccgattat gcatcaggat tggctgaacg gcaaagaatt taaatgccgc   1020
```

```
gtgaacagcg cggcgtttcc ggcgccgatt gaaaaaacca ttagcaaaac caaaggccgc   1080

ccgaaagcgc cgcaggtgta taccattccg ccgccgaaag aacagatggc gaaagataaa   1140

gtgagcctga cctgcatgat taccgatttt tttccggaag atattaccgt ggaatggcag   1200

tggaacggcc agccggcgga aaactataaa aacacccagc cgattatgga taccgatggc   1260

agctattttg tgtatagcaa actgaacgtg cagaaaagca actgggaagc gggcaacacc   1320

tttacctgca gcgtgctgca tgaaggcctg cataaccatc ataccgaaaa aagcctgagc   1380

catagcccgg gcaaa                                                    1395
```

<210> SEQ ID NO 6
<211> LENGTH: 1395
<212> TYPE: DNA
<213> ORGANISM: Artificial Sequence
<220> FEATURE:
<223> OTHER INFORMATION: Degenerate reverse translation of heavy chain with signal peptide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:

<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (246)..(246)

<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:

<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (618)..(618)

<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:

<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (912)..(912)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (996)..(996)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1035)..(1035)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1047)..(1047)

<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1065)..(1065)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1080)..(1080)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1104)..(1104)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1149)..(1149)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature -continued
<222> LOCATION: (1176)..(1176)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1218)..(1218)
<223> OTHER INFORMATION: n is a, c, g, or t
<220> FEATURE:
<221> NAME/KEY: misc_feature
<222> LOCATION: (1236)..(1236)
<223> OTHER INFORMATION: n is a, c, g, or t
<220> FEATURE:
<221> NAME/KEY: misc_feature
<222> LOCATION: (1242)..(1242)
<223> OTHER INFORMATION: n is a, c, g, or t
<220> FEATURE:
<221> NAME/KEY: misc_feature
<222> LOCATION: (1254)..(1254)
<223> OTHER INFORMATION: n is a, c, g, or t
<220> FEATURE:
<221> NAME/KEY: misc_feature
<222> LOCATION: (1260)..(1260)
<223> OTHER INFORMATION: n is a, c, g, or t
<220> FEATURE:
<221> NAME/KEY: misc_feature
<222> LOCATION: (1263)..(1263)
<223> OTHER INFORMATION: n is a, c, g, or t
<220> FEATURE:
<221> NAME/KEY: misc_feature
<222> LOCATION: (1272)..(1272)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1284)..(1284)
<223> OTHER INFORMATION: n is a, c, g, or t
<220> FEATURE:
<221> NAME/KEY: misc_feature
<222> LOCATION: (1290)..(1290)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1311)..(1311)
<223> OTHER INFORMATION: n is a, c, g, or t
<220> FEATURE:
<221> NAME/KEY: misc_feature
<222> LOCATION: (1314)..(1314)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t
<220> FEATURE:
<221> NAME/KEY: misc_feature
<222> LOCATION: (1326)..(1326)
<223> OTHER INFORMATION: n is a, c, g, or t
<220> FEATURE:

<221> NAME/KEY: misc_feature
<222> LOCATION: (1332)..(1332)
<223> OTHER INFORMATION: n is a, c, g, or t
<220> FEATURE:
<221> NAME/KEY: misc_feature
<222> LOCATION: (1335)..(1335)
<223> OTHER INFORMATION: n is a, c, g, or t
<220> FEATURE:
<221> NAME/KEY: misc_feature
<222> LOCATION: (1338)..(1338)
<223> OTHER INFORMATION: n is a, c, g, or t
<220> FEATURE:
<221> NAME/KEY: misc_feature
<222> LOCATION: (1347)..(1347)
<223> OTHER INFORMATION: n is a, c, g, or t
<220> FEATURE:
<221> NAME/KEY: misc_feature
<222> LOCATION: (1350)..(1350)
<223> OTHER INFORMATION: n is a, c, g, or t
<220> FEATURE:
<221> NAME/KEY: misc_feature
<222> LOCATION: (1365)..(1365)
<223> OTHER INFORMATION: n is a, c, g, or t
<220> FEATURE:
<221> NAME/KEY: misc_feature
<222> LOCATION: (1374)..(1374)
<223> OTHER INFORMATION: n is a, c, g, or t
<220> FEATURE:
<221> NAME/KEY: misc_feature
<222> LOCATION: (1377)..(1377)
<223> OTHER INFORMATION: n is a, c, g, or t
<220> FEATURE:
<221> NAME/KEY: misc_feature
<222> LOCATION: (1380)..(1380)
<223> OTHER INFORMATION: n is a, c, g, or t
<220> FEATURE:
<221> NAME/KEY: misc_feature
<222> LOCATION: (1386)..(1386)
<223> OTHER INFORMATION: n is a, c, g, or t
<220> FEATURE:
<221> NAME/KEY: misc_feature
<222> LOCATION: (1389)..(1389)
<223> OTHER INFORMATION: n is a, c, g, or t
<220> FEATURE:
<221> NAME/KEY: misc_feature
<222> LOCATION: (1392)..(1392)
<223> OTHER INFORMATION: n is a, c, g, or t

<400> SEQUENCE: 6
atggaywsnm gnytnaayyt ngtnttyytn gtnytngtny tnaarggngt nytntgygar 60
gtnaargtng tngarwsngg nggnggnytn gtnmgnccng gnggnwsnyt naarytnwsn 120
tgywsngcnw snggnttyac nttywsnwsn taygcnatgw sntgggtnmg ncaracnccn 180
garaarmgny tngartgggt ngcntayath wsncayggng gnggngayac ntaytayytn 240
gayacngtna arggnmgntt yacnathwsn mgngayaayg cnaaraayws nytntayytn 300
caratgwsnw snytnatgws ngargayacn gcnatgtayt aytgygtnmg nmgnggntay 360
gaytaygayg gngaytaygc natggaytay tggggncarg gnacnwsngt nacngtnwsn 420
wsngcnaara cnacnccncc nwsngtntay ccnytngcnc cnggnwsngc ngcncaracn 480
aaywsnatgg tnacnytngg ntgyytngtn aarggntayt tyccngarcc ngtnacngtn 540
acntggaayw snggnwsnyt nwsnwsnggn gtncayacnt tyccngcngt nytncarwsn 600
gayytntaya cnytnwsnws nwsngtnacn gtnccnwsnw snacntggcc nwsngaracn 660
gtnacntgya aygtngcnca yccngcnwsn wsnacnaarg tngayaaraa rathgtnccn 720
mgngaytgyg gntgyaarcc ntgyathtgy acngtnccng argtnwsnws ngtnttyath 780
ttyccnccna arccnaarga ygtnytnacn athacnytna cnccnaargt nacntgygtn 840
gtngtngaya thwsnaarga ygayccngar gtncarttyw sntggttygt ngaygaygtn 900

-continued gargtncaya cngcncarac ncarccnmgn gargarcart tyaaywsnac nttymgnwsn 960
gtnwsngary tnccnathat gcaycargay tggytnaayg gnaargartt yaartgymgn 1020
gtnaaywsng cngcnttycc ngcnccnath garaaracna thwsnaarac naarggnmgn 1080
ccnaargcnc cncargtnta yacnathccn ccnccnaarg arcaratggc naargayaar 1140
gtnwsnytna cntgyatgat hacngaytty ttyccngarg ayathacngt ngartggcar 1200
tggaayggnc arccngcnga raaytayaar aayacncarc cnathatgga yacngayggn 1260
wsntayttyg tntaywsnaa rytnaaygtn caraarwsna aytgggargc nggnaayacn 1320
ttyacntgyw sngtnytnca ygarggnytn cayaaycayc ayacngaraa rwsnytnwsn 1380
caywsnccng gnaar 1395

<210> SEQ ID NO 7
<211> LENGTH: 1338
<212> TYPE: DNA
<213> ORGANISM: Artificial Sequence
<220> FEATURE:
<223> OTHER INFORMATION: Predicted nucleotide sequence of heavy chain
without signal peptide

<400> SEQUENCE: 7
gaagtgaaag tggtggaaag cggcggcggc ctggtgcgcc cgggcggcag cctgaaactg 60
agctgcagcg cgagcggctt tacctttagc agctatgcga tgagctgggt gcgccagacc 120
ccggaaaaac gcctggaatg ggtggcgtat attagccatg gcggcggcga tacctattat 180
ctggataccg tgaaaggccg ctttaccatt agccgcgata acgcgaaaaa cagcctgtat 240
ctgcagatga gcagcctgat gagcgaagat accgcgatgt attattgcgt gcgccgcggc 300
tatgattatg atggcgatta tgcgatggat tattggggcc agggcaccag cgtgaccgtg 360
agcagcgcga aaaccacccc gccgagcgtg tatccgctgg cgccgggcag cgcggcgcag 420
accaacagca tggtgaccct gggctgcctg gtgaaaggct attttccgga accggtgacc 480
gtgacctgga acagcggcag cctgagcagc ggcgtgcata cctttccggc ggtgctgcag 540
agcgatctgt ataccctgag cagcagcgtg accgtgccga gcagcacctg gccgagcgaa 600
accgtgacct gcaacgtggc gcatccggcg agcagcacca aagtggataa aaaaattgtg 660
ccgcgcgatt gcggctgcaa accgtgcatt tgcaccgtgc cggaagtgag cagcgtgttt 720
atttttccgc cgaaaccgaa agatgtgctg accattaccc tgaccccgaa agtgacctgc 780
gtggtggtgg atattagcaa agatgatccg gaagtgcagt ttagctggtt tgtggatgat 840
gtggaagtgc ataccgcgca gacccagccg cgcgaagaac agtttaacag cacctttcgc 900
agcgtgagcg aactgccgat tatgcatcag gattggctga acggcaaaga atttaaatgc 960
cgcgtgaaca gcgcggcgtt tccggcgccg attgaaaaaa ccattagcaa aaccaaaggc 1020
cgcccgaaag cgccgcaggt gtataccatt ccgccgccga aagaacagat ggcgaaagat 1080
aaagtgagcc tgacctgcat gattaccgat ttttttccgg aagatattac cgtggaatgg 1140
cagtggaacg gccagccggc ggaaaactat aaaaacaccc agccgattat ggataccgat 1200
ggcagctatt ttgtgtatag caaactgaac gtgcagaaaa gcaactggga agcgggcaac 1260
acctttacct gcagcgtgct gcatgaaggc ctgcataacc atcataccga aaaaagcctg 1320
agccatagcc cgggcaaa 1338

<210> SEQ ID NO 8
<211> LENGTH: 1338

<212> TYPE: DNA
<213> ORGANISM: Artificial Sequence
<220> FEATURE:
<223> OTHER INFORMATION: Degenerate reverse translation of heavy chain without signal peptide
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:

<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)

<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:

<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (738)..(738)

<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (864)..(864)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:

<221> NAME/KEY: misc_feature
<222> LOCATION: (984)..(984)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1035)..(1035)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1053)..(1053)
<223> OTHER INFORMATION: n is a, c, g, or t
<220> FEATURE:
<221> NAME/KEY: misc_feature
<222> LOCATION: (1056)..(1056)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1107)..(1107)
<223> OTHER INFORMATION: n is a, c, g, or t
<220> FEATURE:
<221> NAME/KEY: misc_feature
<222> LOCATION: (1119)..(1119)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1161)..(1161)
<223> OTHER INFORMATION: n is a, c, g, or t
<220> FEATURE:
<221> NAME/KEY: misc_feature
<222> LOCATION: (1179)..(1179)
<223> OTHER INFORMATION: n is a, c, g, or t
<220> FEATURE:
<221> NAME/KEY: misc_feature
<222> LOCATION: (1185)..(1185)
<223> OTHER INFORMATION: n is a, c, g, or t
<220> FEATURE:
<221> NAME/KEY: misc_feature
<222> LOCATION: (1197)..(1197)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1227)..(1227)
<223> OTHER INFORMATION: n is a, c, g, or t
<220> FEATURE:
<221> NAME/KEY: misc_feature
<222> LOCATION: (1233)..(1233)
<223> OTHER INFORMATION: n is a, c, g, or t
<220> FEATURE:
<221> NAME/KEY: misc_feature
<222> LOCATION: (1242)..(1242)
<223> OTHER INFORMATION: n is a, c, g, or t
<220> FEATURE:
<221> NAME/KEY: misc_feature
<222> LOCATION: (1254)..(1254)
<223> OTHER INFORMATION: n is a, c, g, or t
<220> FEATURE:
<221> NAME/KEY: misc_feature
<222> LOCATION: (1257)..(1257)

<223> OTHER INFORMATION: n is a, c, g, or t
<220> FEATURE:
<221> NAME/KEY: misc_feature
<222> LOCATION: (1263)..(1263)
<223> OTHER INFORMATION: n is a, c, g, or t
<220> FEATURE:
<221> NAME/KEY: misc_feature
<222> LOCATION: (1269)..(1269)
<223> OTHER INFORMATION: n is a, c, g, or t
<220> FEATURE:
<221> NAME/KEY: misc_feature
<222> LOCATION: (1275)..(1275)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1281)..(1281)
<223> OTHER INFORMATION: n is a, c, g, or t
<220> FEATURE:
<221> NAME/KEY: misc_feature
<222> LOCATION: (1290)..(1290)
<223> OTHER INFORMATION: n is a, c, g, or t
<220> FEATURE:
<221> NAME/KEY: misc_feature
<222> LOCATION: (1293)..(1293)
<223> OTHER INFORMATION: n is a, c, g, or t
<220> FEATURE:
<221> NAME/KEY: misc_feature
<222> LOCATION: (1308)..(1308)
<223> OTHER INFORMATION: n is a, c, g, or t
<220> FEATURE:
<221> NAME/KEY: misc_feature
<222> LOCATION: (1317)..(1317)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t
<220> FEATURE:
<221> NAME/KEY: misc_feature
<222> LOCATION: (1323)..(1323)
<223> OTHER INFORMATION: n is a, c, g, or t
<220> FEATURE:
<221> NAME/KEY: misc_feature
<222> LOCATION: (1329)..(1329)
<223> OTHER INFORMATION: n is a, c, g, or t
<220> FEATURE:
<221> NAME/KEY: misc_feature
<222> LOCATION: (1332)..(1332)
<223> OTHER INFORMATION: n is a, c, g, or t
<220> FEATURE:
<221> NAME/KEY: misc_feature
<222> LOCATION: (1335)..(1335)
<223> OTHER INFORMATION: n is a, c, g, or t

<400> SEQUENCE: 8
gargtnaarg tngtngarws nggnggnggn ytngtnmgnc cnggnggnws nytnaarytn 60
wsntgywsng cnwsnggntt yacnttywsn wsntaygcna tgwsntgggt nmgncaracn 120
ccngaraarm gnytngartg ggtngcntay athwsncayg gnggnggnga yacntaytay 180
ytngayacng tnaarggnmg nttyacnath wsnmgngaya aygcnaaraa ywsnytntay 240
ytncaratgw snwsnytnat gwsngargay acngcnatgt aytaytgygt nmgnmgnggn 300
taygaytayg ayggngayta ygcnatggay taytggggnc arggnacnws ngtnacngtn 360
wsnwsngcna aracnacncc nccnwsngtn tayccnytng cnccnggnws ngcngcncar 420
acnaaywsna tggtnacnyt nggntgyytn gtnaarggnt ayttyccnga rccngtnacn 480
gtnacntgga aywsnggnws nytnwsnwsn ggngtncaya cnttyccngc ngtnytncar 540
wsngayytnt ayacnytnws nwsnwsngtn acngtnccnw snwsnacntg gccnwsngar 600
acngtnacnt gyaaygtngc ncayccngcn wsnwsnacna argtngayaa raarathgtn 660
ccnmgngayt gyggntgyaa rccntgyath tgyacngtnc cngargtnws nwsngtntty 720
athttyccnc cnaarccnaa rgaygtnytn acnathacny tnacnccnaa rgtnacntgy 780
gtngtngtng ayathwsnaa rgaygayccn gargtncart tywsntggtt ygtngaygay 840
gtngargtnc ayacngcnca racncarccn mgngargarc arttyaayws nacnttymgn 900
wsngtnwsng arytnccnat hatgcaycar gaytggytna ayggnaarga rttyaartgy 960
mgngtnaayw sngcngcntt yccngcnccn athgaraara cnathwsnaa racnaarggn 1020
mgnccnaarg cnccncargt ntayacnath ccnccnccna argarcarat ggcnaargay 1080
aargtnwsny tnacntgyat gathacngay ttyttyccng argayathac ngtngartgg 1140
cartggaayg gncarccngc ngaraaytay aaraayacnc arccnathat ggayacngay 1200
ggnwsntayt tygtntayws naarytnaay gtncaraarw snaaytggga rgcnggnaay 1260
acnttyacnt gywsngtnyt ncaygarggn ytncayaayc aycayacnga raarwsnytn 1320
wsncaywsnc cnggnaar 1338

<210> SEQ ID NO 9
<211> LENGTH: 702
<212> TYPE: DNA
<213> ORGANISM: Artificial Sequence
<220> FEATURE:
<223> OTHER INFORMATION: Degenerate reverse translation of heavy chain
with signal peptide

<400> SEQUENCE: 9
atgaaaagcc agacccaggt gtttgtgttt ctgctgctgt gcgtgagcgg cgcgcatggc 60
agcattgtga tgacccagac cccgaaattt ctgctggtga gcgcgggcga tcgcgtgacc 120
attacctgca aagcgagcca gagcgtgagc aacgcggtgg cgtggtttca gcagaaaccg 180
ggccagagcc cgaaactgct gatttatttt gcgagcaacc gctttaccgg cgtgccggat 240
cgctttaccg gcagcggcta tggcaccgat tttaccttta ccattagcac cgtgcagccg 300
gaagatctgg cggtgtattt ttgccagcag gattataaca gcccgtttac ctttggcagc 360
ggcaccaaac tggaaattaa acgcgcggat gcggcgccga ccgtgagcat tttttccgccg 420 agcagcgaac agctgaccag cggcggcgcg agcgtggtgt gctttctgaa caacttttat 480
ccgcgcgata ttaacgtgaa atggaaaatt gatggcagcg aacgccagaa cggcgtgctg 540
aacagctgga ccgatcagga tagcaaagat agcacctata gcatgagcag caccctgacc 600
ctgaccaaag atgaatatga acgccataac agctatacct gcgaagcgac ccataaaacc 660
agcaccagcc cgattgtgaa aagctttaac cgcaacgaat gc 702

<210> SEQ ID NO 10
<211> LENGTH: 702
<212> TYPE: DNA
<213> ORGANISM: Artificial Sequence
<220> FEATURE:
<223> OTHER INFORMATION: Degenerate reverse translation of light chain
with signal peptide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:

<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (213)..(213)

<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:

<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (651)..(651)

<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t

<400> SEQUENCE: 10
atgaarwsnc aracncargt nttygtntty ytnytnytnt gygtnwsngg ngcncayggn 60
wsnathgtna tgacncarac nccnaartty ytnytngtnw sngcnggnga ymgngtnacn 120
athacntgya argcnwsnca rwsngtnwsn aaygcngtng cntggttyca rcaraarccn 180
ggncarwsnc cnaarytnyt nathtaytty gcnwsnaaym gnttyacngg ngtnccngay 240
mgnttyacng gnwsnggnta yggnacngay ttyacnttya cnathwsnac ngtncarccn 300
gargayytng cngtntaytt ytgycarcar gaytayaayw snccnttyac nttyggnwsn 360
ggnacnaary tngarathaa rmgngcngay gcngcnccna cngtnwsnat httyccnccn 420
wsnwsngarc arytnacnws nggnggngcn wsngtngtnt gyttyytnaa yaayttytay 480
ccnmgngaya thaaygtnaa rtggaarath gayggnwsng armgncaraa yggngtnytn 540
aaywsntgga cngaycarga ywsnaargay wsnacntayw snatgwsnws nacnytnacn 600
ytnacnaarg aygartayga rmgncayaay wsntayacnt gygargcnac ncayaaracn 660
wsnacnwsnc cnathgtnaa rwsnttyaay mgnaaygart gy 702

<210> SEQ ID NO 11
<211> LENGTH: 642
<212> TYPE: DNA
<213> ORGANISM: Artificial Sequence
<220> FEATURE:
<223> OTHER INFORMATION: Predicted nucleotide sequence of light chain
without signal peptide

<400> SEQUENCE: 11
agcattgtga tgacccagac cccgaaattt ctgctggtga gcgcgggcga tcgcgtgacc 60
attacctgca aagcgagcca gagcgtgagc aacgcggtgg cgtggtttca gcagaaaccg 120
ggccagagcc cgaaactgct gatttatttt gcgagcaacc gctttaccgg cgtgccggat 180
cgctttaccg gcagcggcta tggcaccgat tttaccttta ccattagcac cgtgcagccg 240

```
gaagatctgg cggtgtattt ttgccagcag gattataaca gcccgtttac ctttggcagc    300

ggcaccaaac tggaaattaa acgcgcggat gcggcgccga ccgtgagcat ttttccgccg    360

agcagcgaac agctgaccag cggcggcgcg agcgtggtgt gctttctgaa caacttttat    420

ccgcgcgata ttaacgtgaa atggaaaatt gatggcagcg aacgccagaa cggcgtgctg    480

aacagctgga ccgatcagga tagcaaagat agcacctata gcatgagcag caccctgacc    540

ctgaccaaag atgaatatga acgccataac agctatacct gcgaagcgac ccataaaacc    600

agcaccagcc cgattgtgaa aagctttaac cgcaacgaat gc                       642
```

<210> SEQ ID NO 12
<211> LENGTH: 642
<212> TYPE: DNA
<213> ORGANISM: Artificial Sequence
<220> FEATURE:
<223> OTHER INFORMATION: Degenerate reverse translation of light chain without signal peptide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:

<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (285)..(285)

<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:

<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t -continued

```
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t

<400> SEQUENCE: 12

wsnathgtna tgacncarac nccnaartty ytnytngtnw sngcnggnga ymgngtnacn     60

athacntgya argcnwsnca rwsngtnwsn aaygcngtng cntggttyca rcaraarccn    120

ggncarwsnc cnaarytnyt nathtaytty gcnwsnaaym gnttyacngg ngtnccngay    180

mgnttyacng gnwsnggnta yggnacngay ttyacnttya cnathwsnac ngtncarccn    240

gargayytng cngtntaytt ytgycarcar gaytayaayw snccnttyac nttyggnwsn    300

ggnacnaary tngarathaa rmgngcngay gcngcnccna cngtnwsnat httyccnccn    360

wsnwsngarc arytnacnws nggnggngcn wsngtngtnt gyttyytnaa yaayttytay    420

ccnmgngaya thaaygtnaa rtggaarath gayggnwsng armgncaraa yggngtnytn    480

aaywsntgga cngaycarga ywsnaargay wsnacntayw snatgwsnws nacnytnacn    540

ytnacnaarg aygartayga rmgncayaay wsntayacnt gygargcnac ncayaaracn    600

wsnacnwsnc cnathgtnaa rwsnttyaay mgnaaygart gy                       642
```